United States Patent
Bai et al.

(10) Patent No.: US 9,639,973 B2
(45) Date of Patent: May 2, 2017

(54) MUON TOMOGRAPHY IMAGING IMPROVEMENT USING OPTIMIZED LIMITED ANGLE DATA

(71) Applicant: Decision Sciences International Corporation, Poway, CA (US)

(72) Inventors: Chuanyong Bai, Poway, CA (US); Joel Kindem, San Diego, CA (US); Weidong Luo, San Diego, CA (US); Matthew Steiger, El Cajon, CA (US); Sean Simon, Vista, CA (US); Michael James Sossong, Ramona, CA (US)

(73) Assignee: Decision Sciences International Corporation, Poway, CA (US)

( * ) Notice: Subject to any disclaimer, the term of this patent is extended or adjusted under 35 U.S.C. 154(b) by 14 days.

(21) Appl. No.: 14/678,921

(22) Filed: Apr. 3, 2015

(65) Prior Publication Data
US 2015/0287237 A1 Oct. 8, 2015

Related U.S. Application Data

(60) Provisional application No. 61/975,704, filed on Apr. 4, 2014.

(51) Int. Cl.
*G06K 9/00* (2006.01)
*G06T 15/08* (2011.01)
(Continued)

(52) U.S. Cl.
CPC .............. *G06T 15/08* (2013.01); *G01V 5/00* (2013.01); *G01V 5/0016* (2013.01); *G06T 11/60* (2013.01)

(58) Field of Classification Search
None
See application file for complete search history.

(56) References Cited

U.S. PATENT DOCUMENTS 7,945,105 B1 5/2011 Jaenisch
8,247,767 B2 8/2012 Morris et al.
(Continued)

FOREIGN PATENT DOCUMENTS

WO 02/067201 A1 8/2002
WO WO 02067201 A1 * 8/2002 ............ G06T 11/006

OTHER PUBLICATIONS

Agostinelli, S., et al., "GEANT4—a simulation tool kit," Nuclear Instruments and Methods in Physics Research A, 506(3):250-303, Jul. 2003.
(Continued)

*Primary Examiner* — Feng Niu
(74) *Attorney, Agent, or Firm* — Perkins Coie LLP

(57) ABSTRACT

Disclosed technology can provide a process for generating reconstructed muon image resolution to optimize the use of the limited angular range muon track data collected by a muon tomography system. In one aspect, a process for improving reconstructed muon image resolution for a volume of interest (VOI) imaged by a muon tomography system includes: collecting raw muon track data of cosmic ray muon tracks passing through the VOI; grouping the raw muon track data into two or more subsets of tracks based on at least one angular distribution of the muon tracks in the raw muon track data; generating a set of images of the VOI based on the two or more subsets of tracks; and combining information from the set of reconstructed images and a reconstructed image based on the full set of the raw muon track data to obtain a resulting reconstructed image of the VOI.

20 Claims, 35 Drawing Sheets

(51) Int. Cl.
  *G06T 11/60* (2006.01)
  *G01V 5/00* (2006.01)

(56) References Cited

U.S. PATENT DOCUMENTS

| | | | | |
|---|---|---|---|---|
| 8,288,721 B2* | 10/2012 | Morris | ................ | G01T 1/18 250/251 |
| 8,565,860 B2* | 10/2013 | Kimchy | ................ | A61B 5/055 250/363.01 |
| 8,575,546 B2* | 11/2013 | Nagamine | ................ | G01B 15/04 250/306 |
| 8,909,325 B2* | 12/2014 | Kimchy | ................ | G01T 1/161 600/407 |
| 2006/0081784 A1 | 4/2006 | Ross et al. | | |
| 2008/0315091 A1* | 12/2008 | Morris | ................ | G01T 1/18 250/307 |
| 2011/0216945 A1* | 9/2011 | Jaenisch | ................ | G01V 5/0008 382/104 |
| 2014/0226003 A1* | 8/2014 | Phaneuf | ................ | H01J 37/222 348/80 |

OTHER PUBLICATIONS

Hock, R.C., "Advances in Cosmic Ray Muon Tomography Reconstruction Algorithms," Master of Science thesis, Florida Institute of Technology, 188 pages, Dec. 2009.

International Search Report and Written Opinion mailed on Jul. 10, 2015 for International Application No. PCT/US2015/024386, filed on Apr. 3, 2015 (12 pages).

Morris, C.L. et al., "Tomographic Imaging with Cosmic Ray Muons," Science and Global Security, 16(1-2):37-53, Oct. 2008.

Schultz, L.J., et al., "Image reconstruction and material Z discrimination via cosmic ray muon radiography," Nuclear Instruments and Methods in Physics Research A, 519(3):687-694, Mar. 2004.

Schultz, L.J., et al., "Statistical Reconstruction for Cosmic Ray Muon Tomography," IEEE Transactions on Image Processing, 16(8):1985-1993, Aug. 2007.

\* cited by examiner

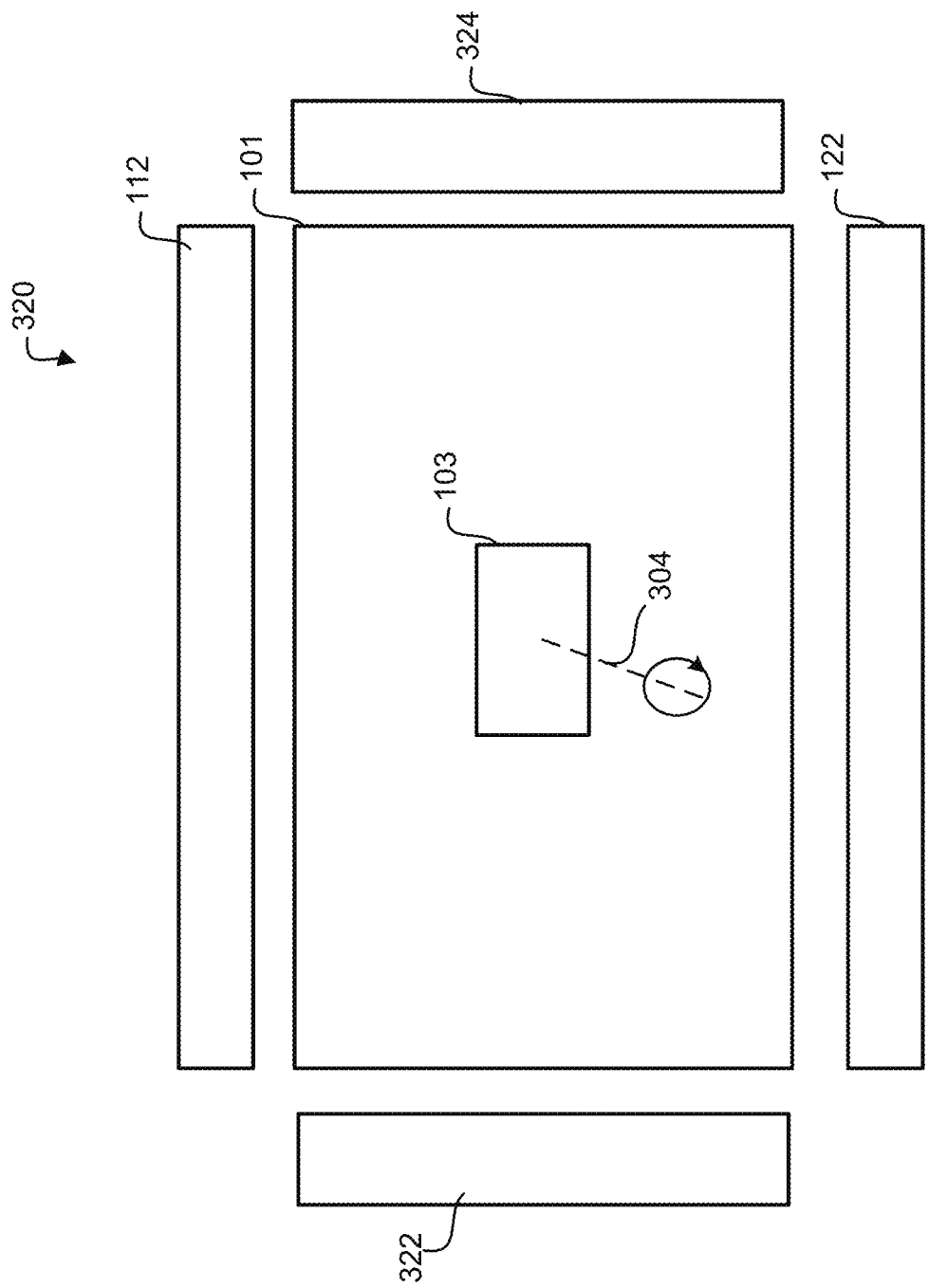

MUON TOMOGRAPHY IMAGING IMPROVEMENT USING OPTIMIZED LIMITED ANGLE DATA

CROSS REFERENCE TO RELATED APPLICATIONS

This patent document claims the benefit of priority of U.S. Provisional Patent Application No. 61/975,704, filed on Apr. 4, 2014. The entire content of the before-mentioned patent application is incorporated by reference as part of the disclosure of this document.

TECHNICAL FIELD

The subject matter described in this disclosure generally relates to systems, devices, and processes for imaging and sensing based on cosmic-ray tomography.

BACKGROUND

Cosmic ray imaging and sensing are techniques which exploit the multiple Coulomb scattering of highly penetrating cosmic ray-produced muons to perform non-destructive inspection of the material without the use of artificial radiation. The Earth is continuously bombarded by energetic stable particles, mostly protons, coming from deep space. These particles interact with atoms in the upper atmosphere to produce showers of particles that include many short-lived pions which decay producing longer-lived muons. Muons interact with matter primarily through the Coulomb force having no nuclear interaction and radiating much less readily than electrons. Such cosmic ray-produced particles slowly lose energy through electromagnetic interactions. Consequently, many of the cosmic ray produced muons arrive at the Earth's surface as highly penetrating charged radiation. The muon flux at sea level is about 1 muon per $cm^2$ per minute.

As a muon moves through material, Coulomb scattering off of the charges of sub-atomic particles perturb its trajectory. The total deflection depends on several material properties, but the dominant effects are the atomic number, Z, of nuclei and the density of the material. The trajectories of muons are more strongly affected by materials that make good gamma ray shielding, such as lead and tungsten, and by special nuclear materials (SNM), such as uranium and plutonium, than by materials that make up more ordinary objects such as water, plastic, aluminum and steel. Each muon carries information about the objects that it has penetrated. The scattering of multiple muons can be measured and processed to probe the properties of these objects. A material with a high atomic number Z and a high density can be detected and identified when the material is located, inside low-Z and medium-Z matter.

Coulomb scattering from atomic nuclei in matter results in a very large number of small angle deflections of charged particles as they transit the matter. In some examples, a correlated distribution function can be used to approximately characterize the displacement and angle change of the trajectory that depends on the density and the atomic charge of the material. As an example, this distribution function can be approximated as a Gaussian distribution. The width of the distribution function is proportional to the inverse of the momentum of the particle and the square root of the real density of material measured in radiation lengths. The correlated distribution function of cosmic ray-produced muons can provide information on materials in the paths of the muons with no radiation dose above the Earth's background and proper detection of such cosmic ray-produced muons can be implemented in a way that is especially sensitive to selected materials to be detected such as good radiation shielding materials.

SUMMARY

Various implementations and examples of the disclosed technology can provide for techniques, devices or systems for generating cosmic-ray based charged particle (e.g., muons) tomography images of a volume of interest (VOI) or a region of interest (ROI), and improving spatial resolution the charged particle tomography images. The generated charged particle tomography images of VOI or ROI are reconstructed from raw track data associated with tracks of charged particles, such as muons, contacting charged particle detectors of an exemplary charged particle tomography system and passing through the VOI or ROI. The disclosed technology can be used to improve the resolution of the generated images of the VOI or ROI by acquiring and processing limited angular range charged particle track data collected by the exemplary charged particle tomography system. Processing the track data can include optimizing such track data. Even though the acquired muon data may have limited zenith angle range, the acquired data can be grouped into different limited angle data subsets for improving image resolutions in desired directions. Generating the images of the VOI or ROI includes performing image reconstruction based on the grouped subsets of the track data to generate multiple images (e.g., a set of images) with resolution enhanced (including optimized) in different directions. Information from the generated set of images based on corresponding subsets of the track data can be combined to improve overall imaging fidelity and the intended applications.

In one aspect, a method for generating charged particle tomography images for a volume of interest (VOI) by a charged particle tomography system is disclosed. The method includes collecting raw track data of tracks of cosmic-ray based charged particles passing through the VOI. The method includes grouping the collected raw track data into subsets of the tracks based on angular distribution of the tracks in the raw track data. The method includes generating a set of images of the VOI based on the grouped subsets of the tracks. The method includes combining information from at least the generated set of images to obtain a resulting image of the VOI.

The method can be implemented in various ways to include one or more of the following features. For example, the method can include generating an image based on full set of the raw track data. The combining can include combining information from the generated image based on the full set of the raw track data along with the information from the generated set of images to obtain the resulting image of the VOI. Grouping the raw track data into the subsets of the tracks based on the angular distribution can include partitioning the raw track data into a first subset corresponding to large zenith angles and a second subset corresponding to small zenith angles. The first subset of tracks can have a zenith angle range from 0 to X and the second subset of tracks can have a zenith angle range from X to 90°, wherein X is between 20° to 45°. The method can include selecting X so that percentage of the tracks in the first subset and percentage of the tracks in the second subset have a predetermined relationship. The predetermined relationship can include the two percentages being substantially equal to each other. A first image of the set of images based on the first subset of the tracks can be associated with an object resolution in a horizontal direction parallel to a detector plane in the charged particle tomography system. A second reconstructed image based on the second subset of the tracks can be associated with an object resolution in a vertical direction perpendicular to a detector plane in the charged particle tomography system. A third reconstructed image based on the full set of the raw track data can be associated with an object resolution in the horizontal direction which is at a level between the object resolutions in the horizontal direction for the first reconstructed image and the second reconstructed image. The third reconstructed image based on the full set of the raw track data can be associated with an object resolution in the vertical direction at a level between the resolutions in the vertical direction for the first reconstructed image and the second reconstructed image.

The method can be implemented to include one or more of the following features. For example, grouping the raw track data into the subsets of the tracks based on the angular distribution can include partitioning the raw track data into a first subset corresponding to azimuthal angles in a first range which are within 45° of an x-direction in a detector plane of the charged particle tomography system. Grouping the raw track data into the subsets of the tracks based on the angular distribution can include partitioning the raw track data into a second subset corresponding to azimuthal angles in a second range which are within 45° of a y-direction in a detector plane of the charged particle tomography system. A first image of the set of images based on the first subset can be associated with an object resolution in the y-direction. A second reconstructed image of the set of images based on the second subset can be associated with an object resolution in the x-direction. Grouping the raw track data into the subsets of the tracks based on the angular distribution can include identifying a subset of the tracks which are substantially perpendicular to a direction û in a detector plane of the charged particle tomography system. An image based on the identified subset of the tracks substantially perpendicular to the direction û can be associated with an object resolution in the û-direction. Grouping the raw track data into the subsets of the tracks based on the angular distribution can include partitioning the raw track data into a first subset corresponding to large zenith angles, a second subset corresponding to small zenith angles, and a third subset corresponding to azimuthal angles. The large zenith angles, the small zenith angles, and the azimuthal angles for the first, second, and third subsets respectively can be within 45° of an x-direction in a detector plane of the charged particle tomography system. Grouping the raw track data into the subsets of the tracks based on the angular distribution can include partitioning the raw track data into a fourth subset corresponding to azimuthal angles which are within 45° of a y-direction in a detector plane of the charged particle tomography system. At least two of the subsets of the tracks share a common cosmic-ray based charged particle track. The cosmic-ray based charge particles can include muons.

In another aspect, a method for generating charged particle tomography image for a volume of interest (VOI) by a charged particle tomography system is disclosed. The method includes collecting raw track data of tracks of cosmic-ray charged particles passing through the VOI. The method includes generating an image of the VOI based on the raw track data. The method includes identifying an orientation of objects in the generated image of the VOI based on the raw track data. The method includes grouping the raw track data into subsets of the tracks based on the identified orientation. The method includes generating a set of images of the VOI based on the subsets of the tracks. The method includes combining information from the generated set of images of the VOI based on the subsets of the tracks and the generated image based on the full set of the track data to obtain a resulting image of the VOI associated with a resolution along the identified orientation.

The method can be implemented in various ways to include one or more of the following features. For example, grouping the raw track data into the subsets of the tracks based on the identified orientation can include identifying a subset of the tracks substantially perpendicular to the identified orientation. An image of the set of images based on the identified subset of tracks substantially perpendicular to the identified orientation can be associated with an object resolution in the identified orientation. Grouping the raw track data into the subsets of the tracks can include partitioning the raw track data into a first subset corresponding to large zenith angles and a second subset corresponding to small zenith angles. The first subset of the tracks can have a zenith angle range from 0 to X and the second subset of the tracks can have a zenith angle range from X to 90° with X being between 20° or 45°. A first image based on the first subset of tracks can provide an improvement of an object resolution in a horizontal direction parallel to a detector plane in the charged particle tomography system; and a second image based on the second subset of tracks can provides an improvement of an object resolution in a vertical direction perpendicular to the detector plane in the charged particle tomography system. Grouping the raw track data into the subsets of tracks can include partitioning the raw muon track data into a first subset corresponding to azimuthal angles in a first range which are within 45° of an x-direction in a detector plane of the muon tomography system; and partitioning the raw muon track data into a second subset corresponding to azimuthal angles in a second range which are within 45° of a y-direction in the detector plane of the charged particle tomography system. A first reconstructed image based on the first subset of tracks can be associated with an object resolution in the y-direction. A second reconstructed image based on the second subset of tracks is associated with an object resolution in the x-direction. The cosmic-ray charged particles can include muons.

In another aspect, a method for performing charged particle tomography imaging of a volume of interest (VOI) by a charged particle tomography system is disclosed. The method includes changing an orientation of the VOI relative to a detector plane of the charged particle tomography system. The method includes collecting raw track data of tracks of cosmic-ray charged particles passing through the VOI at the changed orientation. The method includes generating an image of the VOI based on the collected raw track data at the changed orientation. Changing the orientation of the VOI changes a zenith angular range of the tracks and changes a resolution of the generated image in a vertical direction perpendicular to the detector plane.

The method can be implemented to include one or more of the following features. For example, changing the orientation can include rotating the VOI about a horizontal axis parallel to the detector plane of the charged particle tomography system by an angle between 0 and 90°, or rotating the detector plane about the VOI by an angle between 0 and 90°. The cosmic-ray charged particles can include muons.

In another aspect, a muon tomography system for performing muon imaging of a volume of interest (VOI) exposed to cosmic-ray charged particles includes a first set of position sensitive detectors located on a first position with respect to the VOI to detect events of incident charged particles that contact the first set of position sensitive detectors and enter the VOI. The system includes a second set of position sensitive detectors located on a second position with respect to the VOI opposite to the first position to detect events of outgoing charged particles that exit the VOI and contact the second set of position sensitive detectors. The system includes a rotation mechanism to change an orientation of the VOI with respect to a detector plane of the first and second sets of position sensitive detectors by performing operations including rotating the VOI about a horizontal axis parallel to the detector plane by an angle between 0 and 90°, or rotating the first and second sets of position sensitive detectors about the VOI by an angle between 0 and 90°. The system includes a data collection module for collecting data of cosmic ray muon tracks passing through the VOI at the changed orientation. Changing the orientation changes a zenith angular range and affects an image resolution in a vertical direction perpendicular to the detector plane.

The system can be implemented to include one or more of the following features. For example, the system can include a third set of position sensitive detectors positioned on a third position with respect to the VOI to detect horizontally propagating muons.

BRIEF DESCRIPTION OF THE DRAWINGS

FIG. 3C is a block diagram showing a cross-sectional view of another exemplary charged particle tomography system.

DETAILED DESCRIPTION

Figure 1:
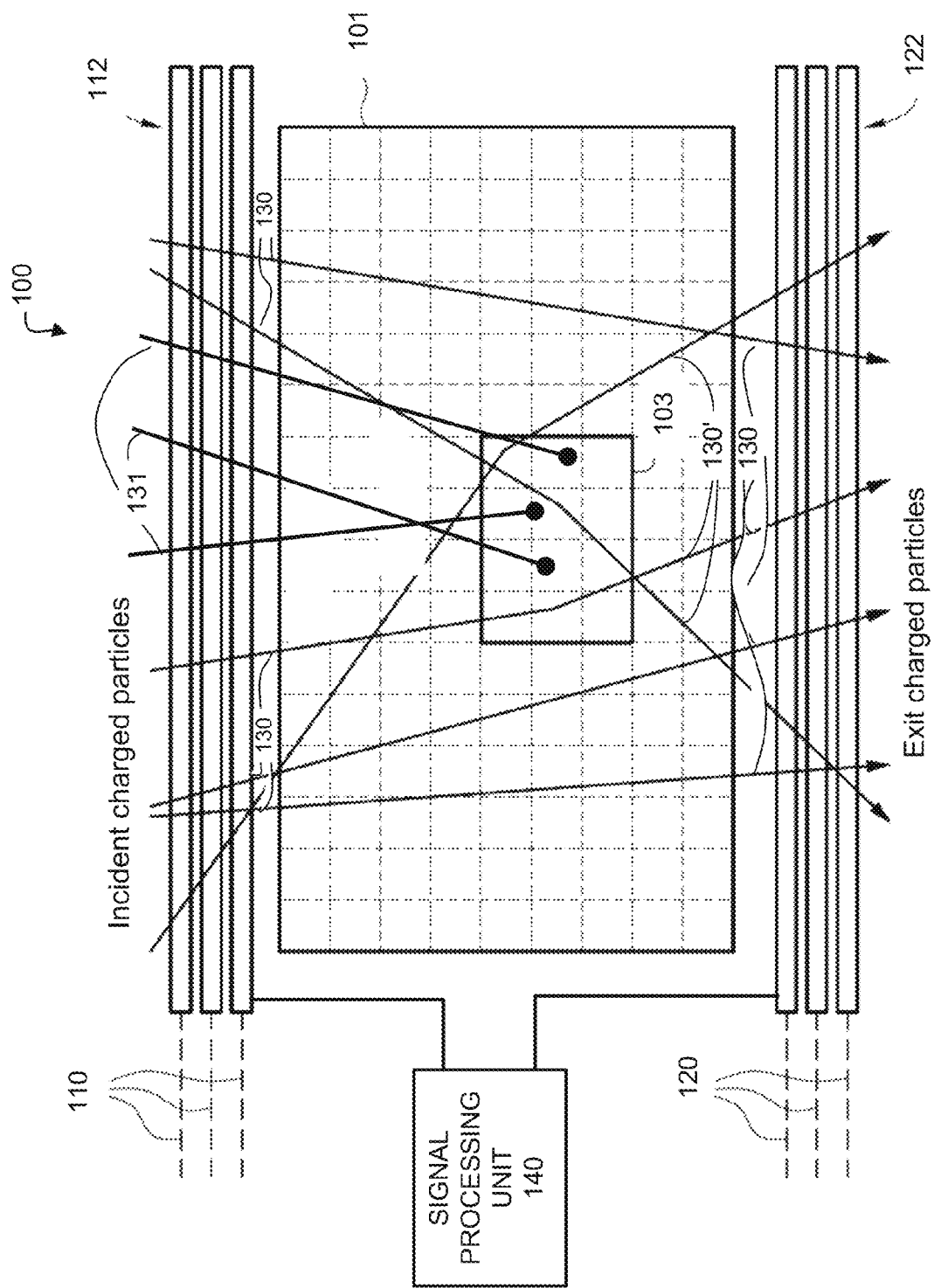
FIG. 1 shows an exemplary cosmic-ray particle tomography system in accordance with some embodiments of the disclosed technology.

In some examples of cosmic ray imaging and sensing, a muon tomography system can be configured to perform tomography of a target object in a ROI or VOI under inspection based on scattering of muons by the target object. For example, muon tomography systems can be used for detecting certain targeted objects, e.g., such as materials that can be used to threaten the public, including smuggled nuclear materials. Muon tomography detector systems can be used jointly with or an alternative to other nuclear material detectors such as gamma or X-ray detectors. Gamma and X-ray detectors operate by directing Gamma and X-ray radiation to a target and measuring penetrated Gamma and X-ray radiation. Shielding of nuclear materials can reduce the count rates in the Gamma and X-ray detectors and reduce the detection performance of Gamma and X-ray detectors. Muon tomography detection systems can be configured to detect shielded nuclear materials and objects.

In an example of a muon tomography detection system, the muon detectors can include an array of drift-tube sensors configured to enable tomographic imaging of a VOI or an ROI using ambient cosmic rays as the illuminating radiation source. Cosmic ray charged particles, e.g., primarily muons and electrons, shower through the VOI or ROI, and measurement of individual particle tracks can be used to reconstruct the three-dimensional distribution of atomic number (Z) and density of materials in the VOI or ROI using particle scattering.

The disclosed technology for improving image resolution of charged particle tomography images include post-processing raw track data (e.g., limited angular range charged particle, such as muon, track data) collected by a charged particle tomography system. Data supporting the disclosed technology include physical data of tungsten blocks acquired and processed using a charged particle (e.g., muon) tomography system. The angular distribution and energy spectrum of charged particles, such as muons, measured by the system were also used to generate simulation data of tungsten blocks of different arrangement (e.g., geometry). The raw charged particle (e.g., muon) track data associated with tracks of charged particles contacting corresponding detector arrays and passing through a VOI or ROI of interest were grouped into subsets of the tracks. The grouping can be based on the zenith angle, for example. A set of images are generated by reconstructing from the subsets of the tracks using multiple distinctive simulation techniques. Image resolution is compared for images associated with different subsets of the tracks. Results show that image resolution is improved in a vertical direction or plane for subsets with greater zenith angles and improved in a horizontal direction or plane for subsets with smaller zenith angles. The overall image resolution may be a compromise of the different subsets. Even though the detected or acquired muon data may have limited zenith angle range, the acquired data can be grouped into different limited angle data subsets for improving image resolutions in desired directions. Reconstruction based on the subset data generates multiple images with resolution optimized in different directions. Using such images jointly can improve overall imaging fidelity and the intended applications.

The cosmic-ray particle detection systems and methods described in this application can be implemented to scan an ROI or VOI to detect presence of certain objects or materials such as nuclear materials and to obtain tomographic information of such objects in various applications including but not limited to inspecting packages, containers, occupied vehicles at security check points, border crossings and other locations for nuclear threat objects that may range from fully assembled nuclear weapons to small quantities of highly shielded nuclear materials. Features described in this application can be used to construct various particle detection systems.

For example, a particle detection system can include an object holding area corresponding to a VOI or ROI for placing an object to be inspected, a first set of position sensitive cosmic-ray particle detectors located at a first location with respect to the object holding area to measure positions and directions of incident cosmic-ray particle towards the object holding area, a second set of position sensitive cosmic-ray particle detectors located on a second location with respect to the object holding area opposite to the first location to measure positions and directions of outgoing cosmic-ray particle exiting the object holding area, and a signal processing unit, which may include, e.g., a microprocessor, to receive data of measured signals of the incoming muons from the first set of position sensitive cosmic-ray particle detectors and measured signals of the outgoing cosmic-ray particle from the second set of position sensitive particle detectors. As an example, each of the first and second sets of particle detectors can be implemented to include drift tubes arranged to allow at least three charged particle positional measurements in a first direction and at least three charged particle positional measurements in a second direction different from the first direction. The signal processing unit can analyze scattering behaviors of the cosmic-ray particles caused by scattering of the cosmic-ray particles in the materials within the object holding area based on the measured incoming and outgoing positions and directions of cosmic-ray particle to obtain a tomographic profile or the spatial distribution of scattering centers within the object holding area. The obtained tomographic profile or the spatial distribution of scattering centers can be used to reveal the presence or absence of one or more objects in the object holding area such as materials with high atomic numbers including nuclear materials or devices. Each position sensitive particle detector in the first and second sets or arrays of particle detectors can be implemented in various configurations, including drift cells such as drift tubes filled with a gas which can be ionized by muons. Such a system can be used to utilize naturally occurring cosmic-ray particles as the particle source for detecting one or more objects in the object holding area.

In applications for portal monitoring, the illustrative embodiments provide an approach to enable robust nuclear material detection at reduced cost and with increased effectiveness. Furthermore, the approach can provide a radiation portal monitor which is capable of determining if a given vehicle or cargo is free of nuclear threats by both measuring the absence of a potential shielded package and the absence of a radiation signature.

The portal monitoring systems of the illustrative embodiments shown in the accompanying drawings employ cosmic ray-produced charged particle tracking with drift tubes. As will be explained in more detail below, the portal monitoring systems utilize drift tubes to enable tracking of charged particles, such as muons and electrons, passing through a volume as well as detection of gamma rays. Advantageously, these portal monitoring systems can effectively provide the combined function of a cosmic ray radiography apparatus with passive or active gamma radiation counter to provide a robust detector for nuclear threats. This eliminates the need for two separate instruments.

Cosmic ray tomography is a technique which exploits the multiple Coulomb scattering of highly penetrating cosmic ray-produced muons to perform non-destructive inspection of the material without the use of artificial radiation. The Earth is continuously bombarded by energetic stable particles, mostly protons, coming from deep space. These particles interact with atoms in the upper atmosphere to produce showers of particles that include many short-lived pions which decay producing longer-lived muons. Muons interact with matter primarily through the Coulomb force having no nuclear interaction and radiating much less readily than electrons. They lose energy only slowly through electromagnetic interactions. Consequently, many of the cosmic ray-produced muons arrive at the Earth's surface as highly penetrating charged radiation. The muon flux at sea level is about 1 muon per cm$^2$ per minute.

As a muon moves through material, Coulomb scattering off of the charges of sub-atomic particles perturb its trajectory. The total deflection depends on several material properties, but the dominant effect is the atomic number, Z, of nuclei. The trajectories are more strongly affected by materials that make good gamma ray shielding (such as lead and tungsten for example) and by special nuclear material (SNM), that is, uranium and plutonium, than by materials that make up more ordinary objects such as water, plastic, aluminum and steel. Each muon carries information about the objects that it has penetrated, and by measuring the scattering of multiple muons one can probe the properties of these objects. A material with a high atomic number Z and a high density can be detected and identified when the material is located, inside low-Z and medium-Z matter.

Coulomb scattering from atomic nuclei results in a very large number of small angle deflections of charged particles as they transit the matter. Enrico Fermi found and solved a transport equation that describes this process to a good approximation. The result is a correlated Gaussian distribution function for the displacement and angle change of the trajectory that depends on the density and the atomic charge of the material. The width of the distribution function is proportional to the inverse of the momentum of the particle and the square root of the real density of material measured in radiation lengths.

Cosmic ray-produced muons and electrons can provide information with no radiation dose above the earth's background and proper detection of such cosmic ray-produced muons and electrons can be implemented in a way that is especially sensitive to good shielding materials. A detection system can be configured to perform tomography of a target object under inspection based on scattering of muons and electrons by the target object. The system can be configured to perform tomography to localize scattering (RC & LS). The tomographic position resolution can be expressed approximately as follows:

$$\Delta x = \theta_{RMS} L$$

where:

$\theta_{RMS}$=the root-mean-square (rms) of the scattering angle, and

L=the size of the volume under the detection by the detection apparatus.

For example, for an exemplary rms scattering angle of 0.02 radian and an apparatus size of 200 cm, the tomographic position resolution is 0.02×200 cm=4 cm.

In one approach, the angular resolution is determined by the following equation based on the Poisson statistics:

$$\frac{\Delta \theta}{\theta} = \frac{1}{\sqrt{2N}}$$

where:

θ=the rms scattering angle,

N=number of cosmic ray-produced muons and/or electrons passing through a region of interest.

For example, the angular resolution for N=100 (corresponding to a 10×10 cm$^2$ resolution element after one minute of counting) is Δθ=0.07θ.

Tomographic methods to reconstruct an image or model of an object from multiple projections taken from different directions, can be implemented in the cosmic ray system to provide a discrete tomographic reconstruction of the volume of interest based on the data provided by the cosmic-ray particles. In some implementations, Monte Carlo simulation techniques can be used to study applications and shorten scanning times. Other stochastic processing methods may also be used in implementing the cosmic ray tomographic imaging described in this application.

The cosmic ray radiography function of the particle detection systems of the embodiments can be more readily understood with reference to examples of detection systems adapted to detect cosmic ray-produced charged particles such as those shown in FIG. 1. Referring initially to FIG. 1, an exemplary detection system 100 utilizing cosmic-ray particles to detect an object includes a set of two or more planes 110 of incoming charged particle detectors 112 arranged above a volume 101 to be imaged for providing the position and angles (i.e., directions in the 3-D space) of incoming charged particle tracks 130 and 131. The incoming charged particle detectors 112 are configured to measure the position and angles of incoming charged particle tracks 130 and 131 with respect to two different directions, e.g., in two orthogonal coordinates along x and y axes. Charged particles (e.g., muons and electrons) pass through the volume 101 where the ROI or VOI 103 may be located and are scattered to an extent dependent upon the material occupying the volume 103 through which they pass. Another set of two or more planes 120 of outgoing charged particle detectors 122 are configured to record outgoing charged particle positions and directions. The drift tubes in detectors 112 and 122 are arranged to allow at least three charged particle positional measurements in a first direction and at least three charged particle positional measurements in a second direction which is different from the first direction and may be orthogonal to the first direction. Side detectors (not shown) may be used to detect more horizontally orientated muon tracks. The scattering angle of each charged particle is computed from the incoming and outgoing measurements.

A signal processing unit 140, e.g., a computer, is provided in the system 100 to receive data of measured signals of the incoming charged particles by the detectors 112 and outgoing charged particles by the detectors 122. This signal processing unit 140 is configured to analyze the scattering of the charged particles in the volume 101 based on the measured incoming and outgoing positions and directions of charged particles to obtain a tomographic profile or the spatial distribution of the scattering density reflecting the scattering strength or radiation length within the volume 101. The obtained tomographic profile or the spatial distribution of the scattering density within the volume 101 can reveal the content of the VOI 103 in the volume 101. FIG. 1 shows drift tube detectors 112 and 122 are located on top and bottom sides of the volume 101. In some implementations, additional drift tube detectors can be implemented on sides of the volume 101 to form a box or four sided structure into which a package, a vehicle or cargo container can enter for scanning by the system.

The processing of measurements for cosmic ray particles in a volume under inspection (e.g., a package, a container or a vehicle) by the signal processing unit 140 for the system 100 in FIG. 1, and other systems described in this application can include reconstructing the trajectory of a charged particle such as a muon or an electron through the volume 101, measuring the momentum of an incoming charged particle based on signals from the detectors 112, measuring the momentum of an outgoing charged particle based on signals from the detectors 122, and determining the spatial distribution of the scattering density of the volume 101. These and other processing results can be used to construct the tomographic profile and measure various properties of the volume 101.

For example, the reconstruction of the trajectory of a charged particle passing through a detector having a set of drift cells can include (a) obtaining hit signals representing identifiers of drift cells hit by charged particles and corresponding hit times; (b) grouping in-time drift cell hits identified as being associated with a track of a particular charged particle passing through said detector; (c) initially estimating a time zero value for a moment of time at which said particular charged particle hits a drift cell; (d) determining drift radii based on estimates of the time zero values, drift time conversion data and the time of the hit; (e) fitting linear tracks to drift radii corresponding to a particular time zero value; and (f) searching and selecting a time-zero value associated with the best of the track fits performed for a particular charged particle and computing error in time-zero and tracking parameter. Such reconstruction of the track based on the time zero fit provides a reconstructed linear trajectory of the charged particle passing through the charged particle detector without having to use fast detectors (such as photomultiplier tubes with scintillator paddles) or some other fast detector which detects the passage of the muon through the apparatus to the nearest few nanoseconds to provide the time-zero.

Also for example, the processing for measuring the momentum of an incoming or outgoing charged particle based on signals from the detectors can include, for example, (a) configuring a plurality of position sensitive detectors to scatter a charged particle passing through the detectors; (b) measuring the scattering of a charged particle in the position sensitive detectors, wherein measuring the scattering comprises obtaining at least three positional measurements of the scattering charged particle; (c) determining at least one trajectory of the charged particle from the positional measurements; and (d) determining at least one momentum measurement of the charged particle from the at least one trajectory. This technique can be used to determine the momentum of the charged particle based on the trajectory of the charged particle which is determined from the scattering of the charged particle in the position sensitive detectors themselves without the use of additional metal plates in the detector.

Also for example, the spatial distribution of the scattering density of the volume can be determined from charged particle tomographic data by: (a) obtaining predetermined charged particle tomography data corresponding to scattering angles and estimated momentum of charged particles passing through object volume; (b) providing the probability distribution of charged particle scattering for use in an image reconstruction technique such as an expectation maximization (ML/EM) technique, the probability distribution being based on a statistical multiple scattering model; (c) determining an estimate of the object volume density, e.g., by determining a substantially maximum likelihood estimate using the expectation maximization (ML/EM) technique; and (d) outputting reconstructed object volume scattering density. The reconstructed object volume scattering density can be used to identify the presence and/or type of object occupying the volume of interest from the reconstructed volume density profile. Various applications include cosmic ray particles tomography for various homeland security inspection applications in which vehicles or cargo can be scanned by a charged particle tracker.

The tomographic processing part of the signal processing unit 140 may be implemented in a computer at the same location as the detectors 112 and 122. Alternatively, the tomographic processing part of the signal processing unit 140 may be implemented in a remote computer that is connected on a computer network such as a private network or a public network such as the Internet.

Further referring to FIG. 1, note that incoming charged particle detectors 112 can detect the X-Y position, angle, speed, and momentum of each of the incident charged particles 130 and 131 entering the volume 101, while outgoing charged particle detectors 122 can detect the X-Y position, angle, speed, and momentum of each of the exiting charged particles 130 passing through volume 101. The signal processing unit 140 is configured to process the position, angle, speed, and momentum data collected by detectors 112 and detectors 122 to match each incident charged particle 130 with a corresponding exiting charged particle 130. The signal processing unit 140 is also configured to process the position, angle, speed, and momentum data collected by detectors 112 and detectors 122 to identify those exiting charged particles 130 that are scattered by VOI 103, such as charged particles 130', and generate a scattering number for the incident charged particles. The signal processing unit 140 is also configured to process the position, angle, speed, and momentum data collected by detectors 112 and detectors 122 to identify incident charged particles 131 which are then stopped inside VOI 103 and generate a stopping number for the incident charged particles.

Further detail of cosmic-ray particle tomography systems which can be used to detect and identify content of a VOI exposed to cosmic ray particles based on the measured scattering and stopping characteristics of the cosmic ray particles is described in U.S. Pat. No. 8,247,767 entitled "PARTICLE DETECTION AND APPLICATIONS IN SECURITY AND PORTAL MONITORING" filed on Oct.

26, 2007, the content of which is incorporated by reference as part of the specification of this application.

Cosmic ray muons typically have a limited zenith angle range at sea level. In tomography using cosmic ray muons, the detected zenith angle range of muons showing on a muon detector can be further reduced by the detector geometry. As a result, image resolution of muon tomography is limited by the range of zenith angles of cosmic ray muons and the flux rate at sea level. Furthermore, low flux rate limits the use of advanced data rebinning and processing techniques to improve image quality. Table 1 lists the zenith angle distribution of muons detected on an exemplary particle tomography system that includes two parallel rectangular detector planes oriented horizontally with a predetermined vertical separation (e.g., 630 cm). The two detector planes are aligned in both horizontal directions while separated from each other in the vertical direction. Examples of detector plane dimension include 779 cm by 1162 cm.

TABLE 1

Angular distribution (percentage in different zenith angle ranges) of cosmic ray muons measured on an exemplary muon tomography system.

| Angle Range | 0°-15° | 0°-24° | 0°-45° | 24°-90° | 45°-90° |
|---|---|---|---|---|---|
| Percentage | 22.8% | 48.1% | 93.4% | 51.9% | 6.6% |

Figure 2A:
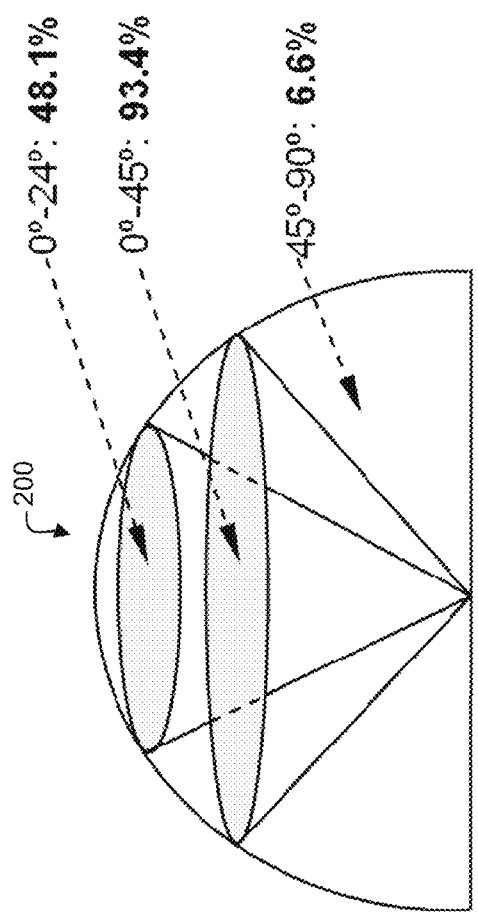
FIG. 2A illustrates the angular flux distribution of cosmic ray muons detected on an exemplary muon tomography system using a spherical sketch in accordance with some embodiments of the disclosed technology.
Figure 2B:
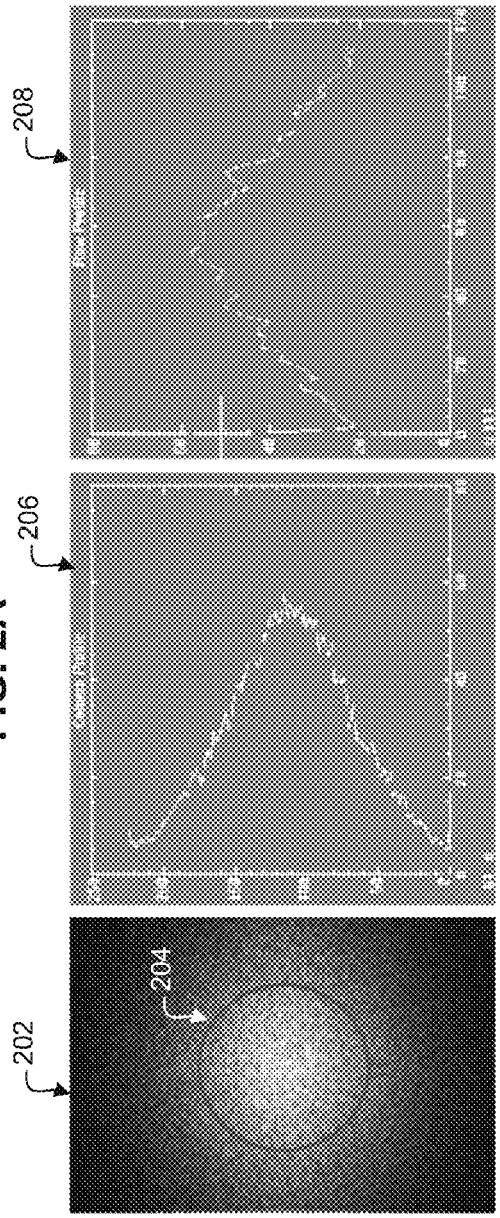
FIG. 2B illustrates the projected image of incident muons on the bottom detector assuming all muons come in through the center of the top detector of the aforementioned exemplary muon tomography system in accordance with some embodiments of the disclosed technology.

FIG. 2A illustrates the angular flux distribution 200 of cosmic ray muons detected on an exemplary muon tomography system using a spherical sketch. For simplicity, the illustration in FIG. 2A ignores the effects of azimuthal asymmetry due to a rectangular detector geometry, as well as the location-dependence on the angular flux distribution within the reconstruction volume of a finite-sized detector. It can be observed that the muons detected on this system are primarily concentrated in zenith angle range from 0° to 45° (including 93.4% of total detected muons). FIG. 2B illustrates a projected image 202 of incident muons on the bottom detector assuming all muons come in through the center of the top detector of the exemplary muon tomography system. The red circle 204 in the left plot identifies the 24° zenith angle boundary. The middle 206 and right 208 plots are profiles of the center column (larger detector dimension) and center row (smaller detector dimension), respectively. This image visually illustrates the angular distribution of the incident muons from the detector's point of view. It has been observed that tomographic reconstructions suffer from considerable vertical blur due to the limited zenith angle range of the detected muons. For vertical clutter scenario, three vertically stacked blocks with a separation of 10 cm between the neighboring blocks showed no visible separation in the reconstructed images.

The disclosed technology demonstrates that given the limited zenith angle range of the detected muons, one can regroup the data into subsets to improve image resolution in a desired direction.

In one aspect, a process for improving reconstructed muon image resolution for a VOI or ROI imaged by a muon tomography system is disclosed. The process includes first collecting raw muon track data of cosmic ray muon tracks passing through the VOI or ROI. The raw muon track data is grouped into two or more subsets of tracks based on at least one angular distribution of the muon tracks in the raw muon track data. For example, the raw muon track data can be grouped by partitioning the raw muon track data into a first subset corresponding to large zenith angles and a second subset corresponding to small zenith angles. The set of images of the VOI or ROI can be generated by using tomography image reconstruction. For example, each image of the set of images can be generated based on a corresponding subset in the two or more subsets of tracks. The information from the set of reconstructed images and a reconstructed image based on the full set of the raw muon track data can be combined to obtain a resulting reconstructed image of the VOI or ROI.

In another aspect, a process for improving reconstructed muon image resolution for VOI or ROI imaged by a muon tomography system is disclosed. The process includes collecting raw muon track data of cosmic ray muon tracks passing through the VOI or ROI. An image of the VOI or ROI is generated by performing image reconstruction using the raw muon track data. An orientation of the objects in the reconstructed image is identified along which direction the resolution is to be improved. The raw muon track data is grouped into two or more subsets of tracks based on the identified orientation. A set of images of the VOI or ROI are generated using image reconstruction. For example, each image of the set of images can be generated based on a corresponding subset in the two or more subsets of tracks. The information from the set of reconstructed images and the reconstructed image based on the full set of the raw muon track data can be combined to obtain a resulting reconstructed image of the VOI or ROI with an improved resolution along the identified orientation.

In yet another aspect, a process for performing muon imaging to improve reconstructed muon image resolution for a VOI or ROI imaged by a muon tomography system is disclosed. The disclosed process includes changing an orientation of the VOI or ROI relative to a detector plane of the charged particle tomography system. For example, the VOI or ROI can be rotated about a horizontal axis parallel to a detector plane of the muon tomography system by an angle between 0 and 90°. The data of cosmic ray muon tracks passing through the VOI or ROI at the rotated position can be collected. An image of the VOI or ROI can be generated using image reconstruction based on the collected muon track data at the rotated position. Rotating the VOI or ROI around the horizontal axis effectively increases the zenith angular range of the detected muon tracks, thereby improving the reconstructing image resolution in the vertical direction perpendicular to the detector plane. In some implementations, the sets or arrays of particle detectors can be rotated with respect to the VOI or ROI (i.e., the object holding area) to achieve the same change of the orientation of the VOI or ROI relative to a detector plane of the charged particle tomography system.

Figure 3A:
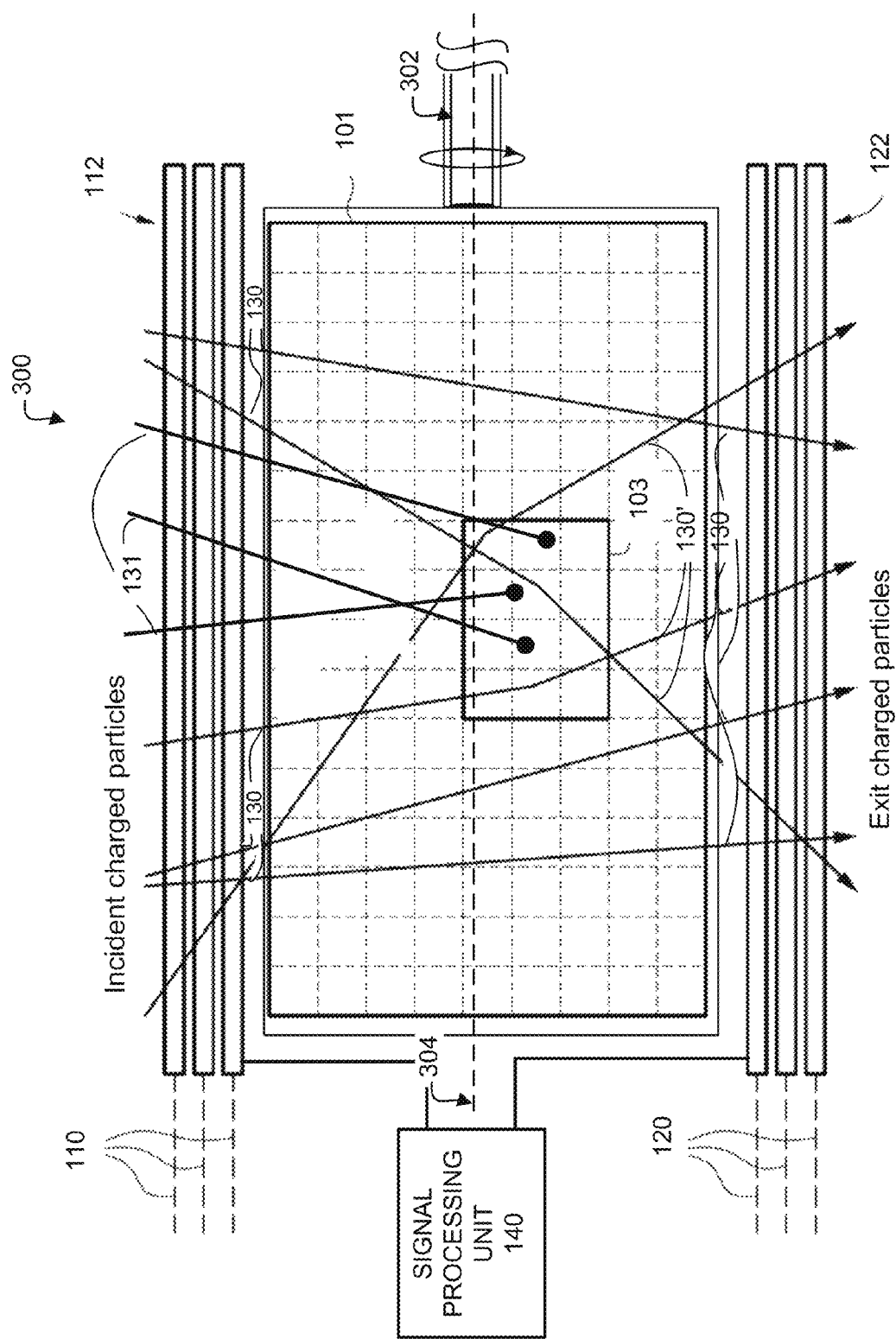
FIG. 3A is a block diagram of an exemplary charged particle tomography system capable of providing a change of an orientation of the VOI or ROI relative to a detector plane of the charged particle tomography system.

FIG. 3A is a block diagram of an exemplary charged particle tomography system 300 capable of providing a change of an orientation of the VOI or ROI relative to a detector plane of the charged particle tomography system. System 300 of FIG. 3A is substantially similar to the system 100 of FIG. 1 but adds a rotating mechanism 302 to rotate the VOI or ROI around a horizontal axis. The rotating mechanism 302 can be implemented using a number of mechanical devices such as a rotating shaft attached to the volume 101 (i.e., an object holding area) to rotate the volume 101 around a horizontal axis 304.

Figure 3B:
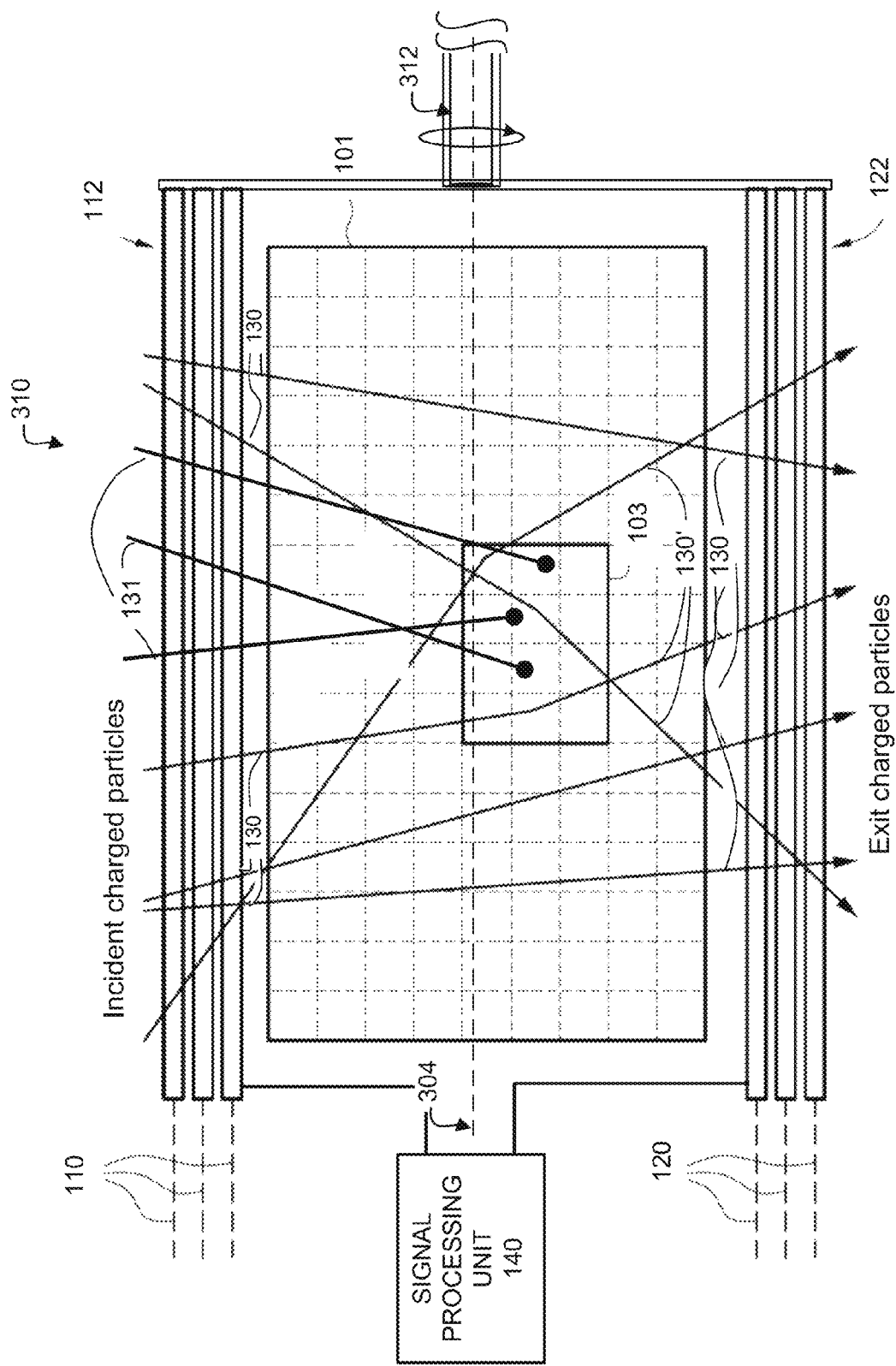
FIG. 3B is a block diagram of another exemplary charged particle tomography system capable of providing a change of an orientation of the VOI or ROI relative to a detector plane of the charged particle tomography system.

FIG. 3B is a block diagram of another exemplary charged particle tomography system 310 capable of providing a change of an orientation of the VOI or ROI relative to a detector plane of the charged particle tomography system. System 310 of FIG. 3B is substantially similar to the system 300 of FIG. 3A but includes a rotating mechanism 312 attached to the sets or arrays of detectors 112 and 122 to rotate the sets or arrays of detectors 112 and 122 around the VOI or ROI and effectively around the horizontal axis 304. The rotating mechanism 312 can be implemented using a number of mechanical devices such as a rotating shaft attached to the sets or arrays of detectors 112 and 122 to rotate the sets or arrays of detectors 112 and 122 around the horizontal axis 304.

FIG. 3C is a block diagram showing a cross-sectional view of another exemplary charged particle tomography system 320. System 320 is substantially similar to system 100 of FIG. 1 but adds an additional pair of detector arrays 322 and 324 at opposite locations with respect to the volume 101. Rather than rotating the volume 101 or the detector arrays 122 and 122 about the horizontal axis 304 (show as projecting out of the plane of the volume 101 in FIG. 3C), the additional pair of detector arrays 322 and 324 at opposite locations with respect to the volume 101 are used to obtain images of the volume 101 at the side surfaces of the volume in addition to the top and bottom surfaces.

Figure 3D:
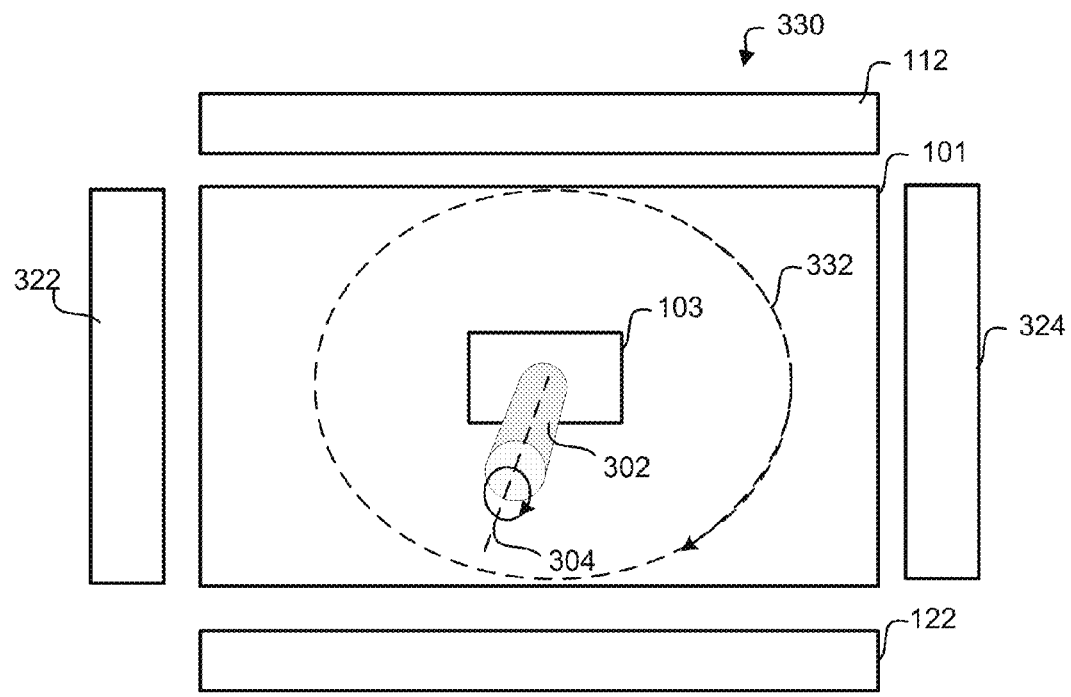
FIG. 3D is a block diagram showing a cross-sectional view of another exemplary charged particle tomography system.

FIG. 3D is a block diagram showing a cross-sectional view of another exemplary charged particle tomography system 330. System 330 is substantially similar to system 320 of FIG. 3C but adds but adds a rotating mechanism 302 (similar to system 300 in FIG. 3A) to rotate the VOI or ROI around a horizontal axis. The rotating mechanism 302 can be implemented using a number of mechanical devices such as a rotating shaft attached to the volume 101 (i.e., an object holding area) to rotate the volume 101 around a horizontal axis 304. The system 330 includes a first set of position sensitive detectors 112 located on a first side of the VOI (volume 101) to detect events of incident charged particles that penetrate the first set of position sensitive detectors to enter the VOI; and a second set of position sensitive detectors 122 located on a second side of the VOI opposite to the first side to detect events of outgoing charged particles exiting the VOI. The system further includes a rotation mechanism 302 configured to rotate the VOI about a horizontal axis 304 parallel to a detector plane (with respect to the top and bottom detector arrays 112 and 122) of the muon tomography system by an angle between 0 and 90°. The system also includes a data collection module for collecting data of cosmic ray muon tracks passing through the VOI at a rotated position of the VOI. Note that rotating the VOI around the horizontal axis effectively increases the detected muon zenith angular range, thereby improving reconstructing image resolution in the vertical direction perpendicular to the detector plane. The system may include a third set of position sensitive detectors 322 positioned on a side of the muon tomography system to detect horizontally propagating muons, thereby increasing a zenith angular range of the collected muon track data. The system can further include a fourth set of position sensitive detectors 324 positioned on a side opposite to the third set of position sensitive detectors 322.

Figure 3E:
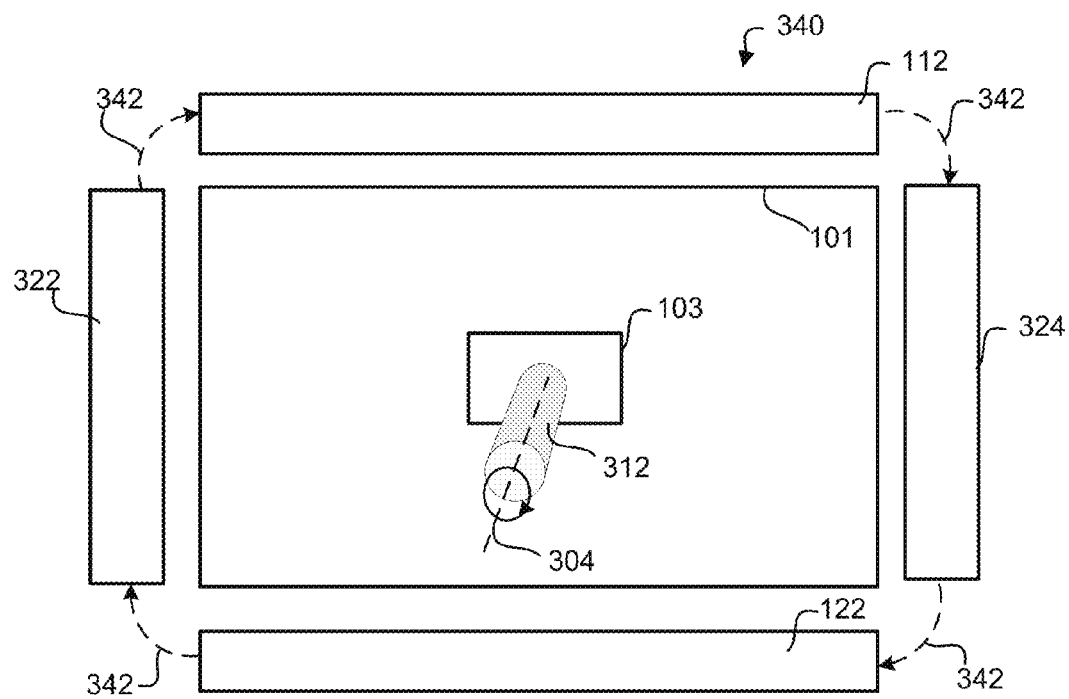
FIG. 3E is a block diagram showing a cross-sectional view of another exemplary charged particle tomography system.

FIG. 3E is a block diagram showing a cross-sectional view of another exemplary charged particle tomography system 340. System 340 is substantially similar to system 320 of FIG. 3C but adds but adds a rotating mechanism 312 (similar to system 310 in FIG. 3B) attached to the sets or arrays of detectors 112 and 122 (also the sets or arrays of detectors 322 and 324) to rotate the sets or arrays of detectors 112 and 122 (also the sets or arrays of detectors 322 and 324) around the VOI or ROI and effectively around the horizontal axis 304. The rotating mechanism 312 can be implemented using a number of mechanical devices such as a rotating shaft attached to the sets or arrays of detectors 112 and 122 (also the sets or arrays of detectors 322 and 324) to rotate the sets or arrays of detectors 112 and 122 (also the sets or arrays of detectors 322 and 324) around the horizontal axis 304. The system 340 includes a first set of position sensitive detectors 112 located on a first side of the VOI (volume 101) to detect events of incident charged particles that penetrate the first set of position sensitive detectors to enter the VOI; and a second set of position sensitive detectors 122 located on a second side of the VOI opposite to the first side to detect events of outgoing charged particles exiting the VOI. The system further includes a rotation mechanism 312 described above. The system also includes a data collection module for collecting data of cosmic ray muon tracks passing through the VOI at a rotated position of the VOI. Note that rotating the VOI around the horizontal axis effectively increases the detected muon zenith angular range, thereby improving reconstructing image resolution in the vertical direction perpendicular to the detector plane. The system may include a third set of position sensitive detectors 322 positioned on a side of the muon tomography system to detect horizontally propagating muons, thereby increasing a zenith angular range of the collected muon track data. The system can further include a fourth set of position sensitive detectors 324 positioned on a side opposite to the third set of position sensitive detectors 322.

To demonstrate the limited angle data optimization concept, a muon tomography system as disclosed in this patent document is used to acquire scattering data from tungsten blocks arranged with specific horizontal and vertical separations. Separately, the angular distribution and energy spectrum of the incident muons detected by the system are also used to generate simulation data. For the specific experiment, each measured and simulated data set is partitioned into two subsets: the first subset of data includes all the muons with zenith angle from 0° to 24° and the second subset of data includes all the muons with zenith angle from 24° to 90°. The first subset accounted for 48.1% of the total muons and the second subset for 51.9%. A reconstruction technique is used to reconstruct each subset of data as well as the overall data set.

Various reconstruction techniques may be used to perform the tomographic image reconstruction. The first one is a PoCA (point of closest approach) technique that first computes the PoCA of the incident and outgoing tracks then assigns the scattering signal to a region centered at the PoCA position, and distributed both parallel and perpendicular to the estimated muon trajectory.

The second technique used for tomographic image reconstruction is an accelerated MLEM (maximum likelihood expectation maximization) technique. In this patent document, the basic MLEM technique is implemented and an acceleration factor is introduced to speed up the reconstruction.

An update equation can be explicitly expressed as:

$$\lambda_j^{(n+1)} = \lambda_j^{(n)}\left(1 + \frac{\sum_i \lambda_j^{(n)} P_{r,i}^2 (D_i^T \Sigma_{Di}^{-1} W_{ij} \Sigma_{Di}^{-1} D_i - \text{Trace}(\Sigma_{Di}^{-1} W_{ij}))}{2M_j}\right),$$

Where $\lambda_j^{(n+1)}$ and $\lambda_j^{(n)}$ are the reconstructed scattering density of voxel j at iteration (n+1) and (n), respectively.

The accelerated MLEM may be expressed as follows:

$$\lambda_j^{(n+1)} = \lambda_j^{(n)}\left(1 + A^{(n)} \frac{\sum_i \lambda_j^{(n)} P_{r,i}^2 (D_i^T \Sigma_{Di}^{-1} W_{ij} \Sigma_{Di}^{-1} D_i - \text{Trace}(\Sigma_{Di}^{-1} W_{ij}))}{2M_j}\right),$$

where $A^{(n)}$ is the acceleration factor at iteration n. In an example implementation, the acceleration factor is initialized to 30 and decreased by a factor of 1.2 for each iteration, but is limited not to go below 1.0. This acceleration technique is expected to speed up the convergence of the basic technique by a factor of 30 as compared to the original MLEM.

The simulation scattering data of tungsten blocks will be evaluated using both of the aforementioned reconstruction techniques, while the measured scattering data of tungsten blocks is reconstructed using the PoCA-based technique.

In one embodiment, to generate the simulation data, a total of 1.5 million particles are simulated, of which 20% are electrons. The electrons are excluded from the analysis, and the tracks of the remaining 1.2 million scattered muons are used in the tomographic reconstruction. Reconstructions are performed on the small zenith angle subset)(0°-24°, large zenith angle subset)(24°-90°, and the complete dataset)(0°-90° independently. Reconstruction parameters are substantially the same for all three data sets. The above procedures are used in the following simulations.

A. Simulation: Isolated Tungsten Blocks

In this simulation, an array of tungsten blocks are arranged in a rectangular water tub wherein the water is used to simulate a uniform low-Z material environment. The simulated tungsten blocks are positioned sufficiently far away from each other so that each block could be considered as isolated from the other blocks. In a particular implementation, the largest tungsten block has a dimension of 50×50×50 cm³. The second largest tungsten block has a dimension of 25×25×25 cm³. Smaller tungsten blocks and thin tungsten sheets are also simulated but not analyzed in this disclosure.

Figure 4:
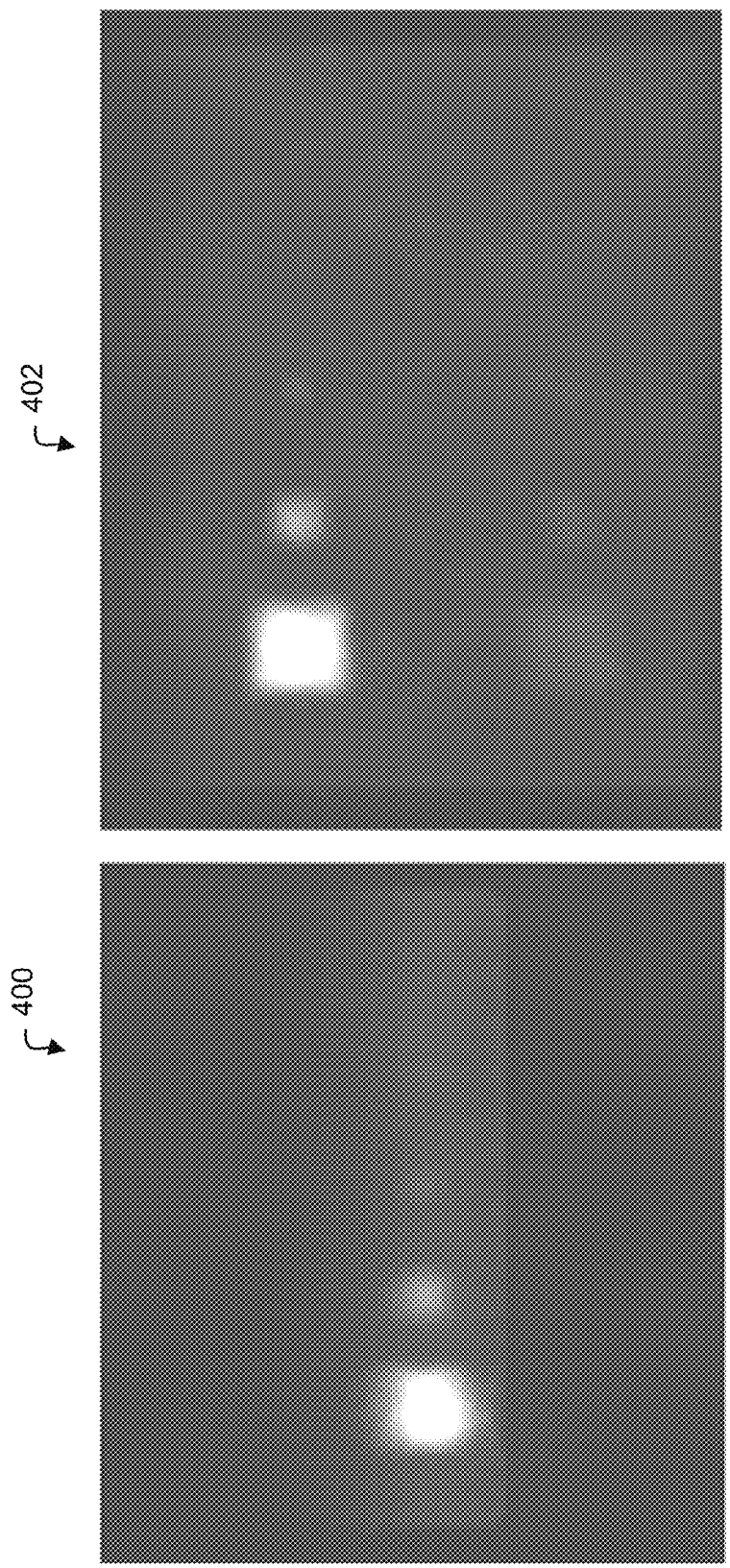
FIG. 4 illustrates the reconstructed images of the tungsten blocks using the distributed PoCA technique in accordance with some embodiments of the disclosed technology.

FIG. 4 illustrates exemplary reconstructed images 400 and 402 of the tungsten blocks using the distributed PoCA technique in accordance with the disclosed technology. The image on the left 400 shows the side view while the one on the right 402 shows the top view. These images illustrate the phantom setup in the simulation. The region of simulated low-Z material (water) surrounding the tungsten blocks is also faintly visible in the images. This simulation setting is used to establish a baseline resolution of the phantom objects. Note that the simulation also includes smaller tungsten blocks and thin tungsten sheets (visible as low contrast squares in the images), however these are not analyzed in this disclosure.

Figure 5:
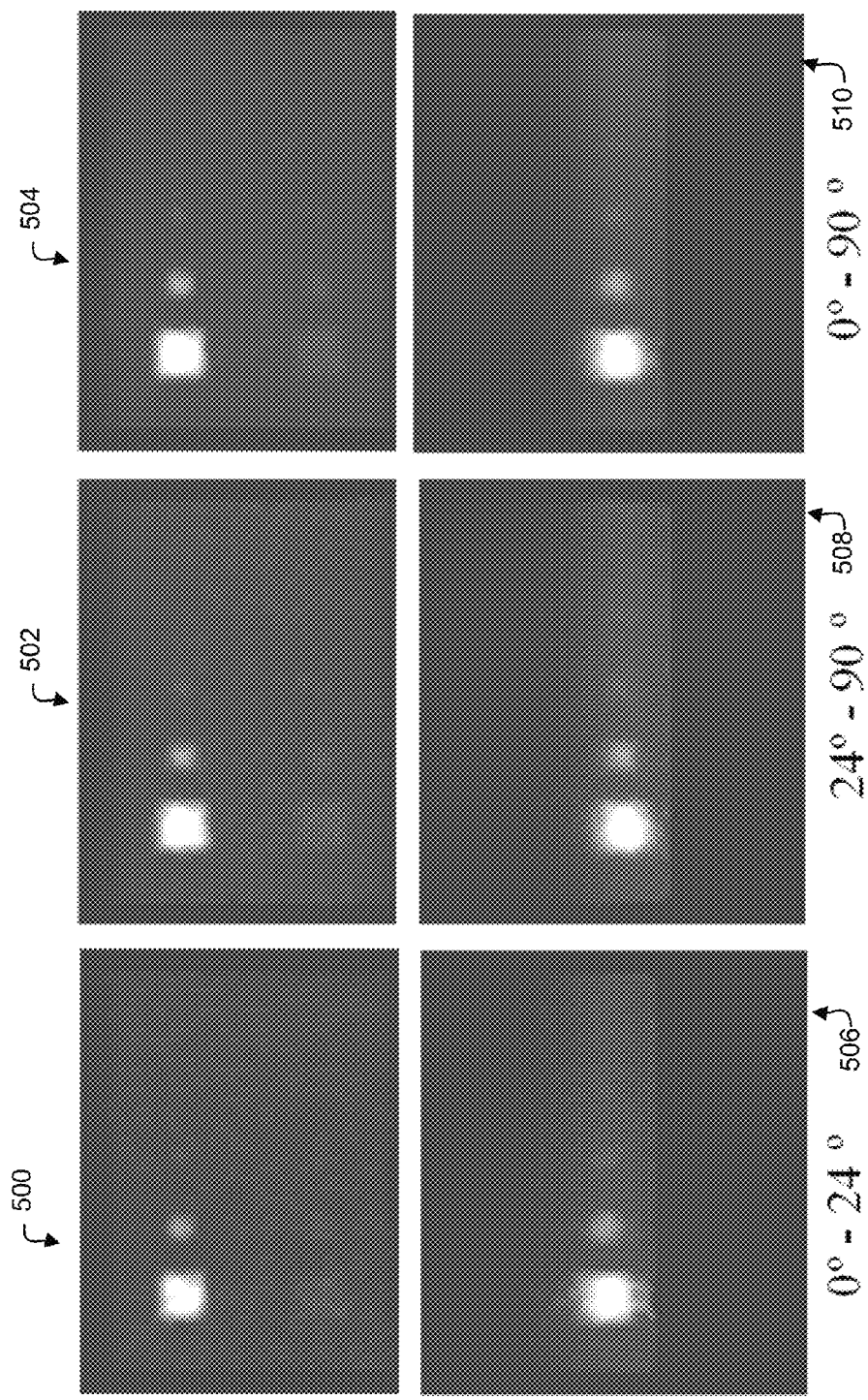
FIG. 5 illustrates the reconstructed images from a small zenith angle subset (left), a large zenith angle subset (middle), and the complete dataset (right), respectively, using the distributed PoCA technique in accordance with some embodiments of the disclosed technology.

FIG. 5 illustrates exemplary reconstructed images from a small zenith angle subset (left) 500 and 506, a large zenith angle subset (middle) 502 and 508, and the complete dataset (right) 504 and 510, respectively, using the distributed PoCA technique in accordance with some embodiments of the disclosed technology. The images in the top row 500, 502, and 504 show the top views while the ones in the bottom row 506, 508, and 510 show the side views. As can be observed from FIG. 5, images from the smaller zenith angle subset (e.g., top left image 500) show better in-plane (i.e., horizontal plane) resolution of the square shape of the tungsten blocks than in the image with greater zenith angle (e.g., top middle image 502). In contrast, images from the larger zenith angle subset (e.g., bottom middle image 508) show better vertical resolution than those from the subset with smaller zenith angle (e.g., bottom left image 506). The differences in resolutions become more obvious for the second largest (25 cm) tungsten block. The resolution in the overall data reconstruction (right images) appears to be in between the two subsets but with better statistics.

Figure 6:
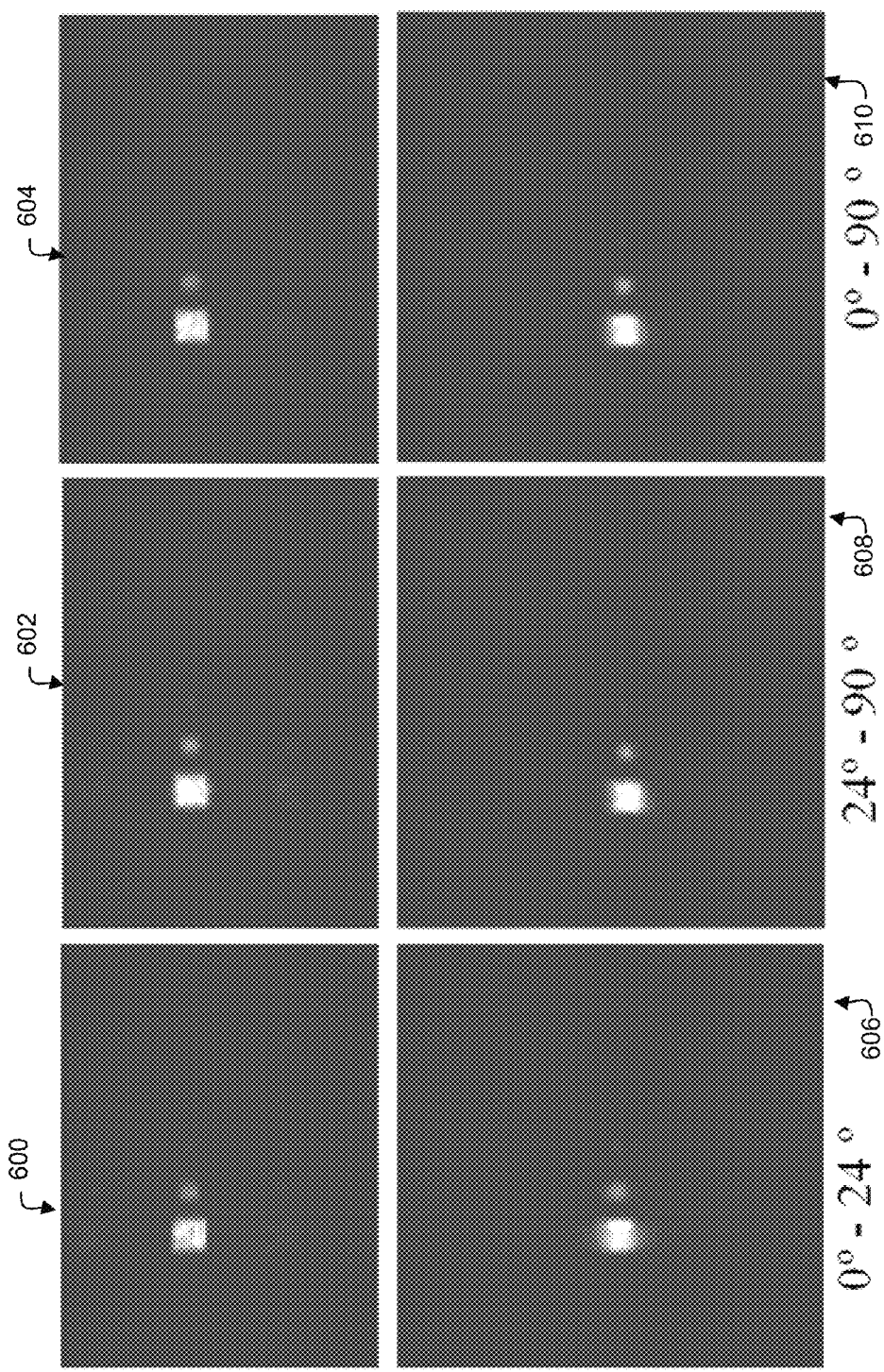
FIG. 6 illustrates the reconstructed images from a small zenith angle subset (left), a large zenith angle subset (middle), and the complete dataset (right), respectively, using the accelerated MLEM technique with five iterations in accordance with some embodiments of the disclosed technology.

FIG. 6 illustrates exemplary reconstructed images from a small zenith angle subset (left) 600 and 606, a large zenith angle subset (middle) 602 and 608, and the complete dataset (right) 604 and 610, respectively, using the accelerated MLEM technique with five iterations in accordance with some embodiments of the disclosed technology. Images showed similar trend as those from the distributed PoCA reconstruction. The images in the top row 600, 602, and 604 show the top views while the ones in the bottom row 606, 608, and 610 show the side views. Image resolution in vertical direction (bottom images 606, 608, and 610) is poorer for the subset with smaller zenith angle (0°-24°) than the subset with larger zenith angle (24°-90°). Image resolution in horizontal plane (top images 600, 602, and 604) is slightly better for the subset with smaller zenith angle (0°-24°) than the subset with larger zenith angle (24°-90°) but the difference is not as obvious as in the distributed PoCA reconstruction. Overall, images in FIG. 6 show similar trend as those from the distributed PoCA reconstruction in FIG. 5.

B. Simulation: Vertically Stacked Tungsten Blocks

In this set of simulations, a set of vertically stacked identical tungsten blocks are simulated with a vertical separation of 15 cm between the block surfaces. This set of simulations is designed to evaluate the vertical resolution of the reconstructed images.

Figure 7:
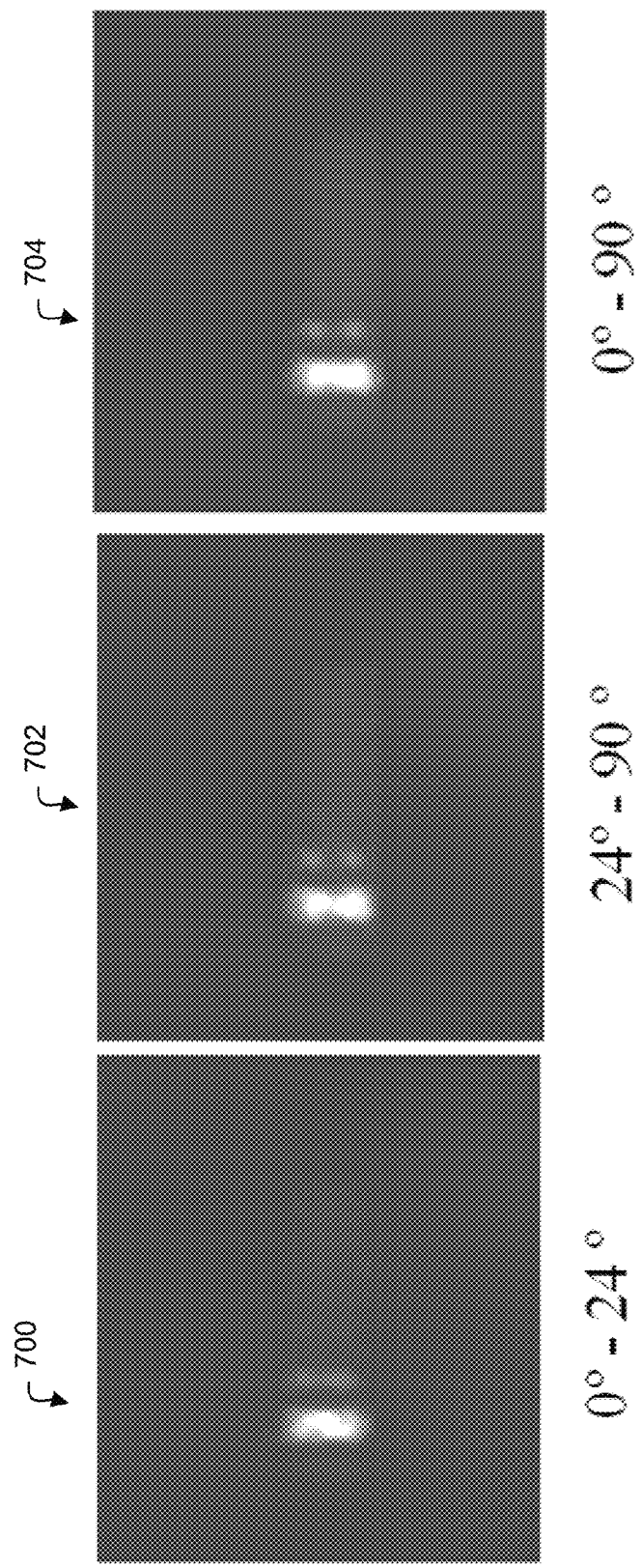
FIG. 7 illustrates the reconstructed images (side view) of vertically stacked tungsten blocks from the two subsets and the overall dataset using the distributed PoCA technique in accordance with some embodiments of the disclosed technology.

FIG. 7 illustrates exemplary reconstructed images 700, 702, and 704 (side view) of vertically stacked tungsten blocks from the two subsets and the overall dataset using the distributed PoCA technique in accordance with some embodiments described herein. Note that the left image 700 with small zenith angle (0°-24°) does not show separation between the two large (50 cm) vertically stacked tungsten blocks and only shows partial separation between the two small (25 cm) blocks. In contrast, the middle image 702 with greater zenith angle (24°-90°) clearly shows the gaps between each pair of blocks. The vertical resolution of the overall image (0°-90°) on the right 704 appears to be in between that of the two subset images.

Figure 8:
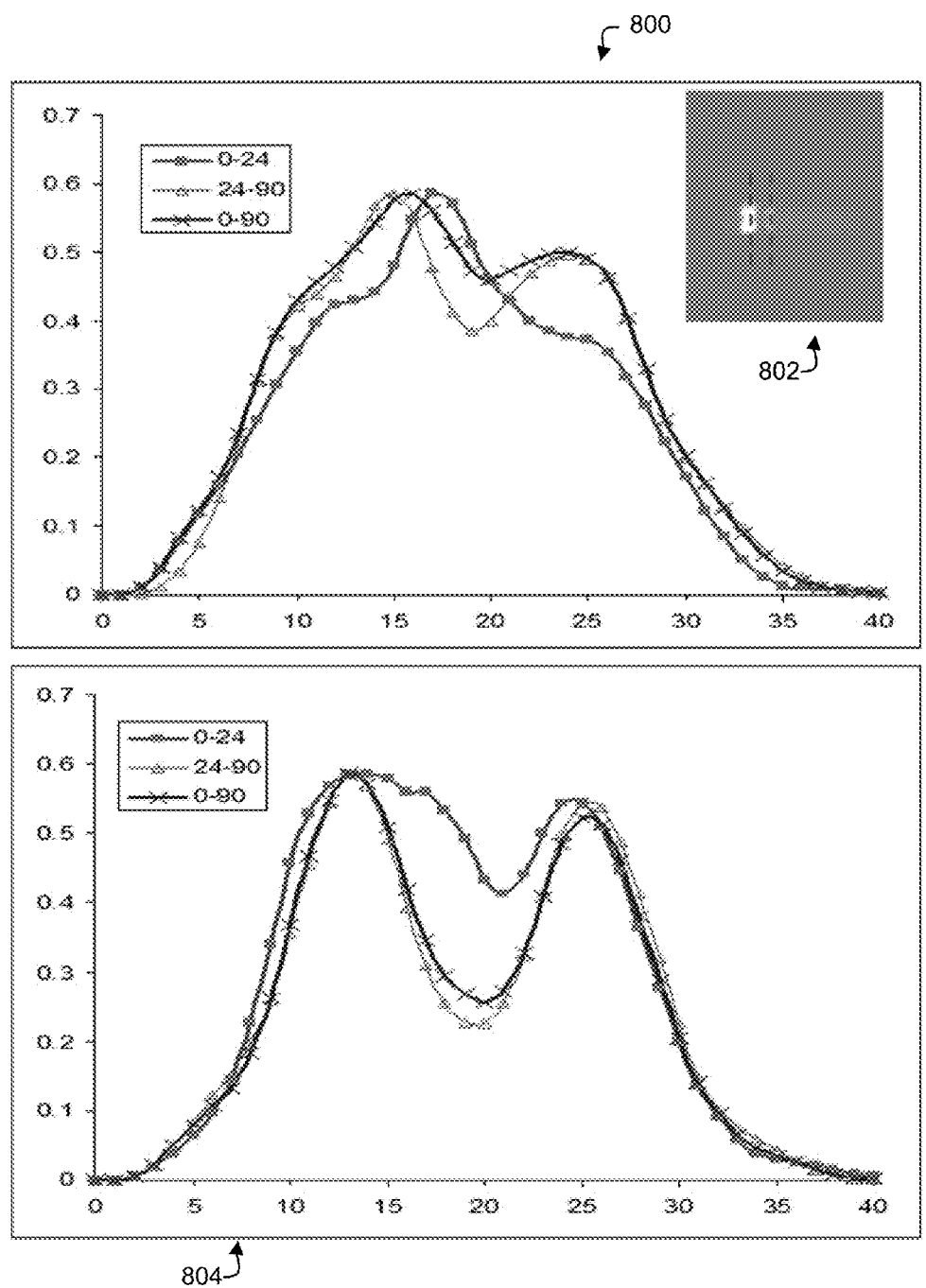
FIG. 8 illustrates the line profiles along the dashed lines in the side view image (top right corner) across the vertically stacked tungsten blocks in accordance with some embodiments of the disclosed technology.

FIG. 8 illustrates exemplary line profiles 800 and 804 along the dashed lines in the side view image (top right corner) 802 across the vertically stacked tungsten blocks in accordance with some embodiments described herein. The top profile 800 is for the line across the large (50 cm) blocks and the bottom profile 804 is for the line across the small (25 cm) blocks. The profiles 800 and 804 show that the subset with greater zenith angle)(24°-90° provides better vertical resolution (separation of the blocks) than the subset with smaller zenith angle)(0°-24°. The overall image resolution is in between that of the two subsets.

Figure 9:
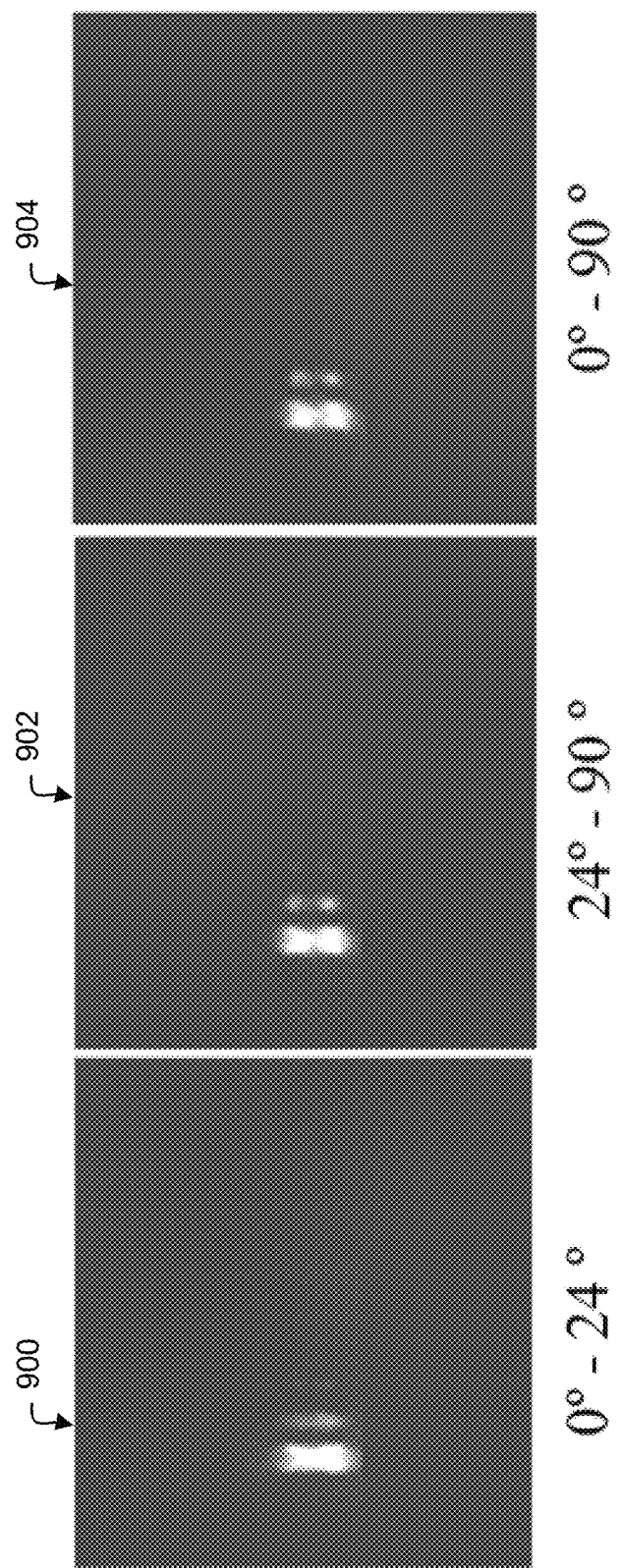
FIG. 9 illustrates the reconstructed images (side view) of the vertically stacked tungsten blocks using the accelerated MLEM reconstruction technique in accordance with some embodiments of the disclosed technology.
Figure 10:
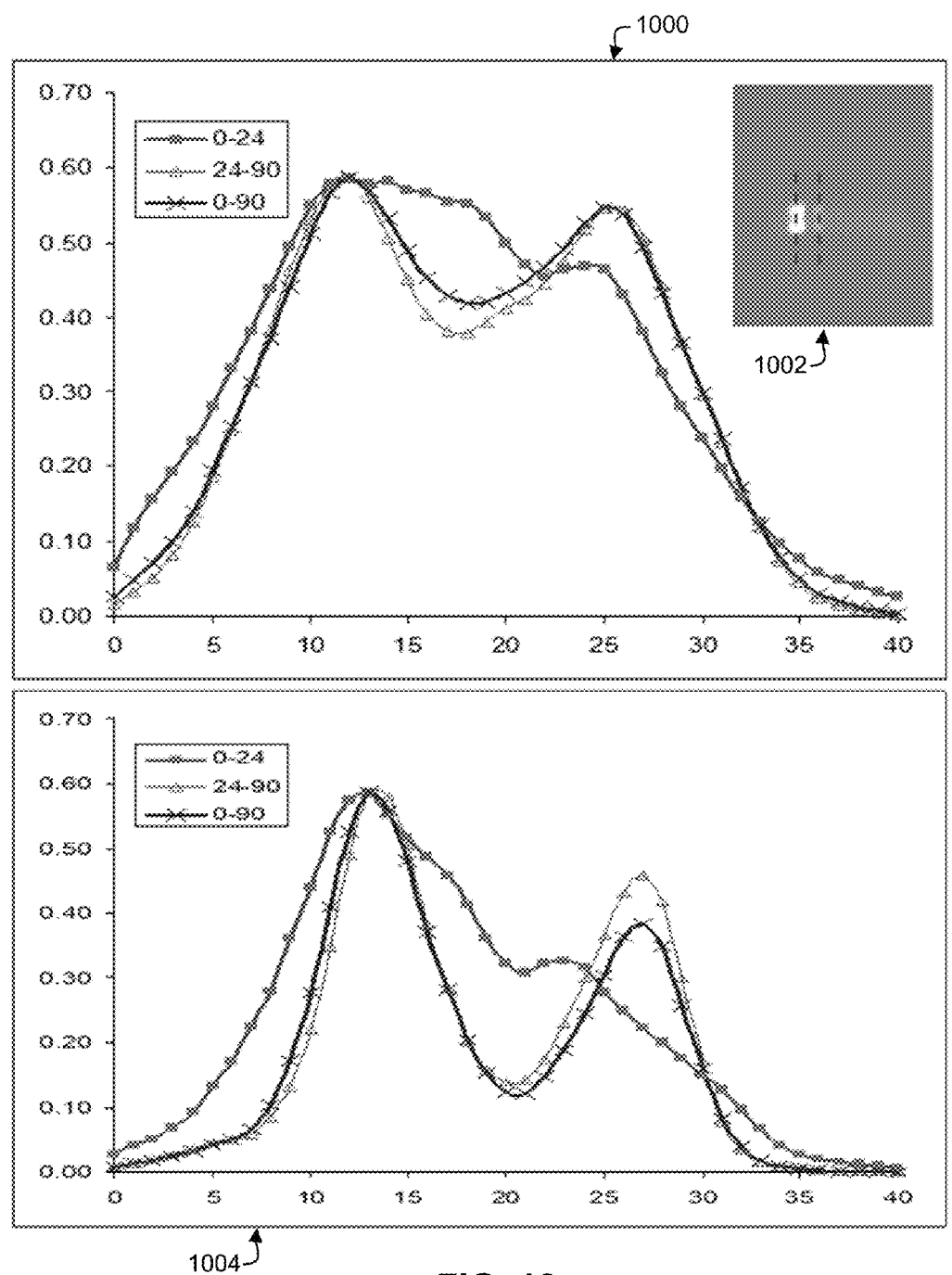
FIG. 10 illustrates the line profiles along dashed lines in the top view image (top right corner) across the vertically stacked tungsten blocks in the MLEM images in FIG. 7 in accordance with some embodiments of the disclosed technology.

FIG. 9 and FIG. 10 are exemplary reconstructed images 900, 902, and 904 and associated profiles 1000 and 1004 using the accelerated MLEM technique on the same vertically stacked blocks as in FIG. 8. Overall, the visual resolution in the image and the gap contrast in the line profiles display similar trend to those in the distributed PoCA reconstruction technique.

More specifically, FIG. 9 illustrates exemplary reconstructed images 900, 902, and 904 (side view) of the vertically stacked tungsten blocks using the accelerated MLEM reconstruction technique in accordance with some embodiments of the disclosed technology. The left image 900 with small zenith angle does not show separation between the two large (50 cm) vertically stacked tungsten blocks and only partial separation between the two small (25 cm) blocks. In contrast, the middle image 904 with greater zenith angle clearly shows the gaps between each pair of blocks. The vertical resolution of the overall image (right) 904 appears to be between that of the two subset images.

FIG. 10 illustrates the associated line profiles 1000 and 1004 along dashed lines in the top view image 1002 (top right corner) across the vertically stacked tungsten blocks in the MLEM images in FIG. 9 in accordance with some embodiments described herein. The top profile 1000 is for the line across the large blocks, and the bottom profile 1004 is for the line across the small blocks. The profiles 1000 and 1004 show that subset with greater zenith angle provides better vertical resolution (separation of the blocks) than the subset with smaller zenith angle. The overall image resolution is in between that of the two subsets.

C. Simulation: Side Stacked Tungsten Blocks

In this set of simulations, identical tungsten blocks are simulated in a side by side configuration in a horizontal plane. The blocks are simulated with 3 horizontal separation distances: 5 cm, 10 cm, and 15 cm in three independent simulations. This set of simulations is designed to evaluate the in-plane (horizontal) resolution of the reconstructed images. The reconstructed images from the two subsets and the overall data showed good separation between the blocks with simulated separation of 15 cm for all the three data sets.

Figure 11:
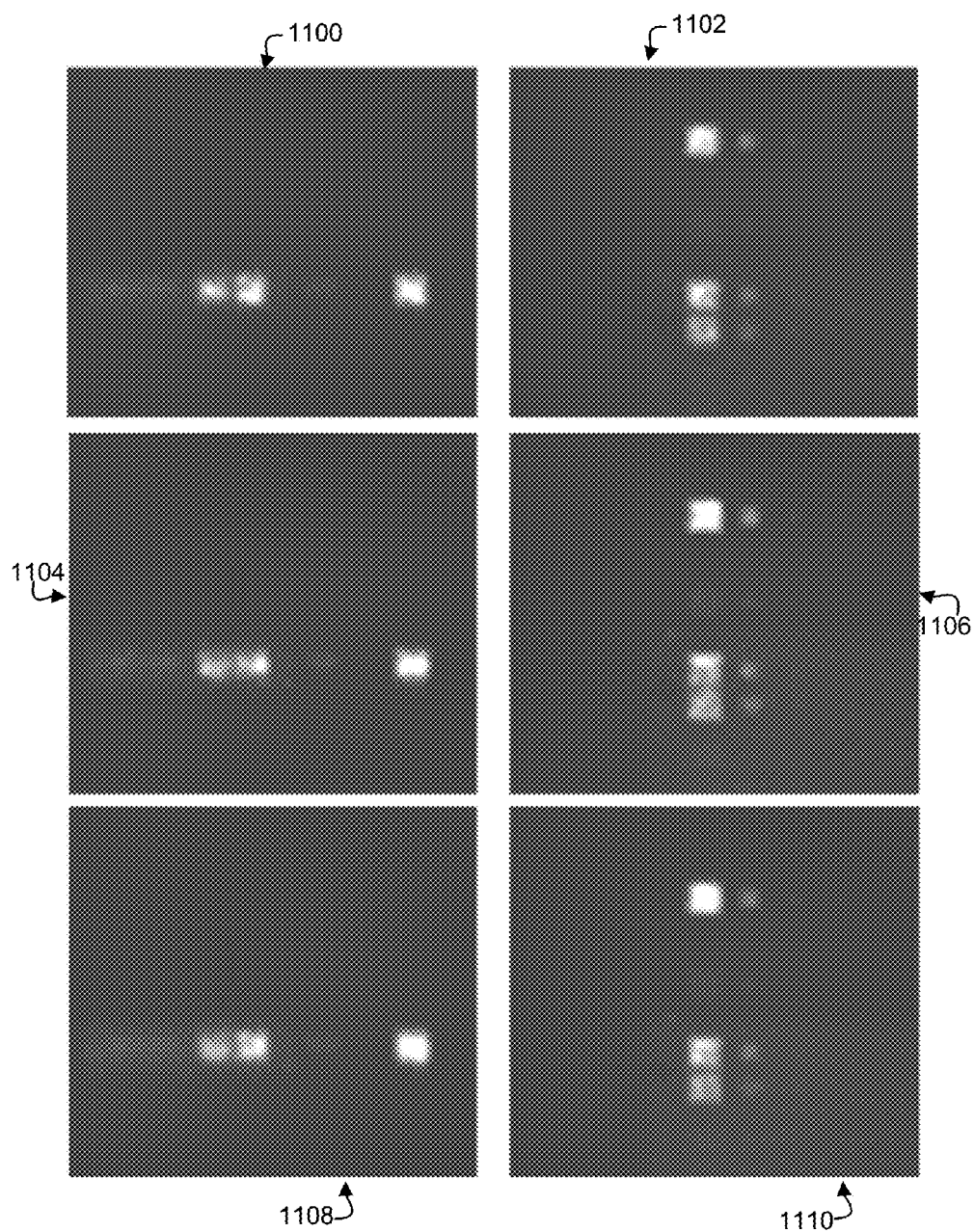
FIG. 11 illustrates the reconstructed images of the tungsten blocks stacked next to each other in the horizontal plane with 10 cm simulated separation using the distributed PoCA reconstruction technique in accordance with some embodiments of the disclosed technology.

FIG. 11 illustrates exemplary reconstructed images of the tungsten blocks stacked next to each other in the horizontal plane with 10 cm simulated separation using the distributed PoCA reconstruction technique in accordance with some embodiments described herein. The images from top to bottom are: subset of 0°-24° (1100 and 1102), subset of 24°-90° (1104 and 1106), and the overall dataset 0°-90° (1108 and 1110). In each row of images, the left one (1100, 1104, or 1108) is the side view and the right one (1102, 1106, or 1110) is the top view. Arrows point to the 10 cm gap between the blocks in horizontal plane. It can be observed from these images that the subset with smaller zenith angle 0°-24° provides the best gap resolution and contrast in the horizontal plane, which is followed by the overall dataset, and finally the 24°-90° subset.

Figure 12:
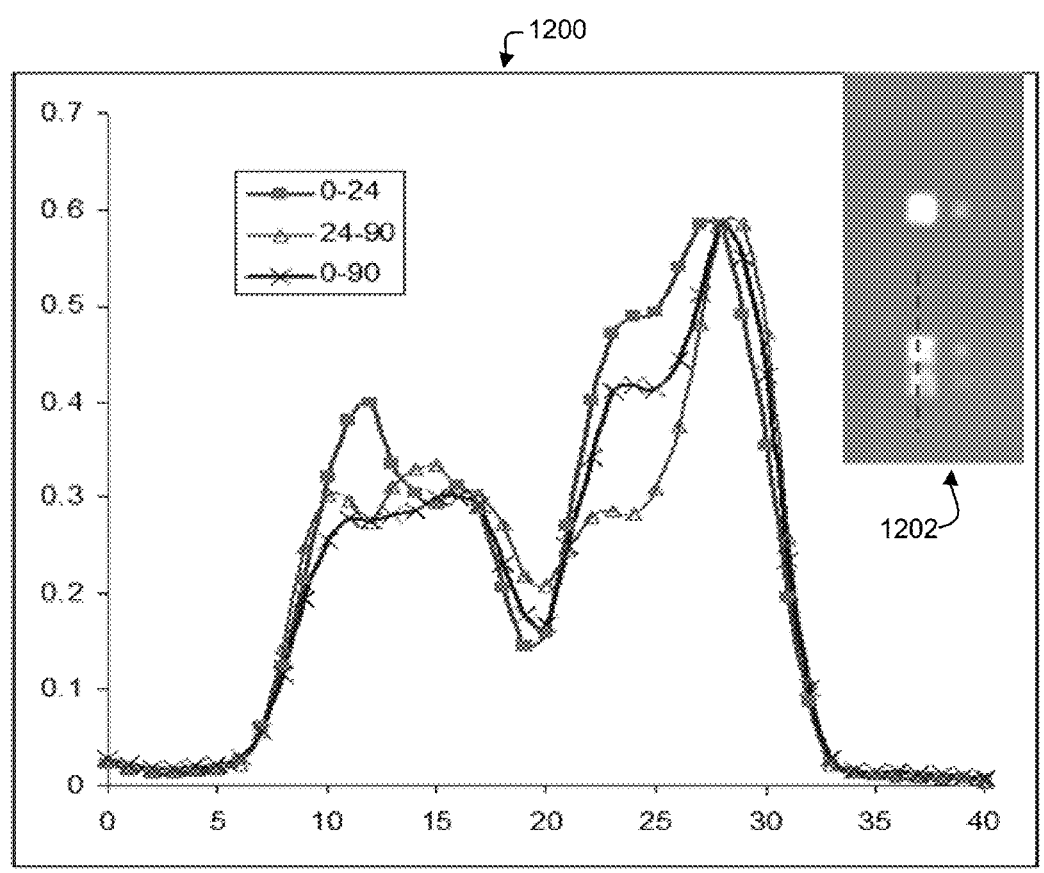
FIG. 12 illustrates the line profiles along the dashed lines in the top right image across the horizontally stacked blocks in the top view in accordance with some embodiments of the disclosed technology.

FIG. 12 illustrates exemplary line profiles 1200 along the dashed lines in the top right image 1202 across the horizontally stacked blocks in the top view in accordance with some embodiments of the disclosed technology. The profiles 1200 show that the subset with small zenith angle)(0°-24° provides best separation and contrast, and the subset with large zenith angle) (24°-90° has the poorest separation and contrast. The overall dataset show separation and contrast in between the small and large zenith angle subsets. The simulation results based on the MLEM technique are similar to the distributed PoCA results. Images and profiles are not shown.

D. Measurement: Tungsten Blocks

Three tungsten blocks were measured in both vertical and side stack arrangements similar to the simulation studies. The actual tungsten blocks, however, were much smaller than in the simulations. Each of the blocks had a dimension of 7.5×7.5×7.5 $cm^3$. The separation between the blocks in the vertical stack arrangement was 15 cm. Because the blocks were significantly smaller than those used in simulation, in the side stack arrangement we chose to use a smaller separation distance of 5 cm to make resolving the horizontally separated blocks more challenging.

Figure 13:
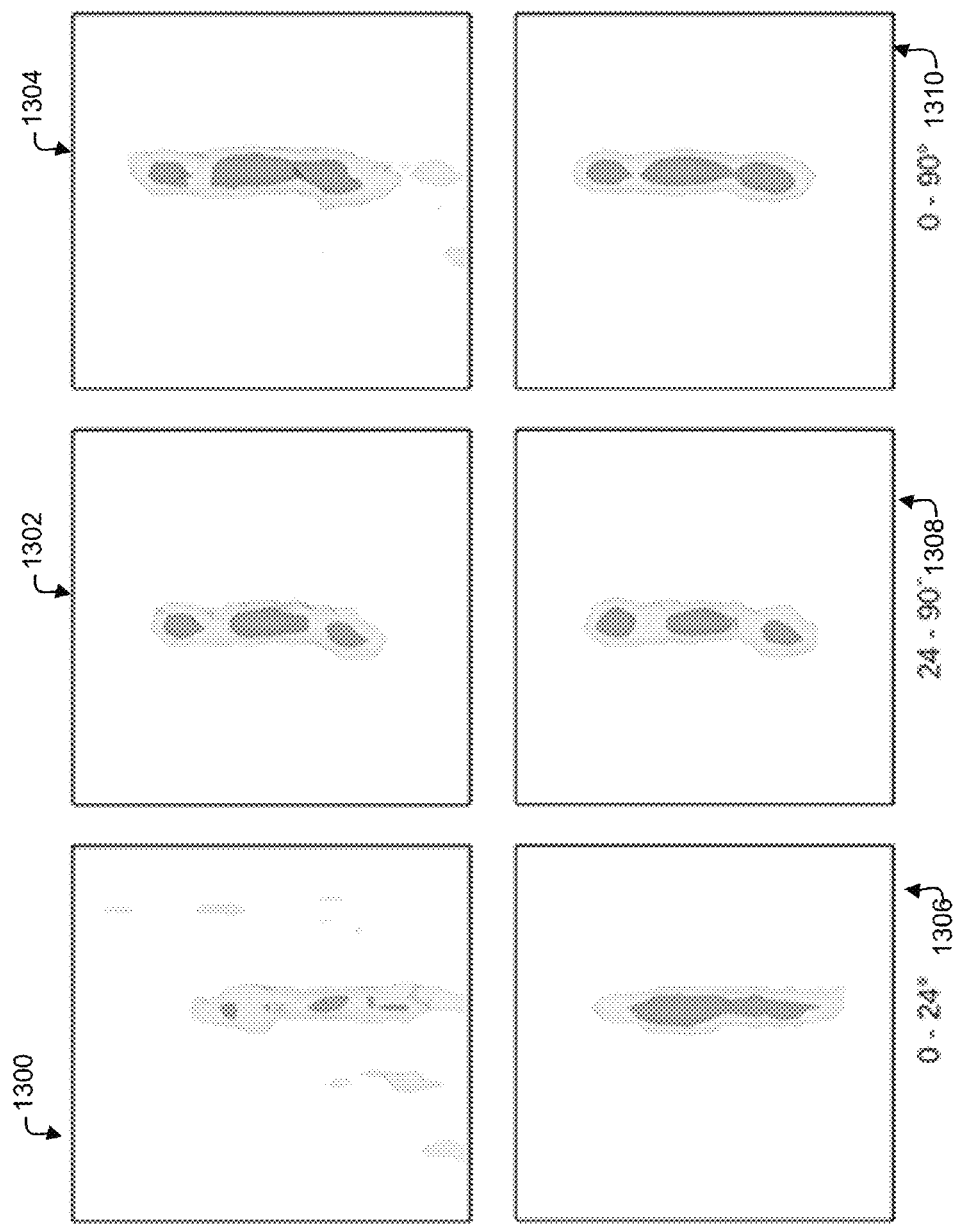
FIG. 13 illustrates the reconstructed images of three vertically stacked 7.5×7.5×7.5 $cm^3$ tungsten blocks (side view) with separation of 15 cm in accordance with some embodiments of the disclosed technology.

FIG. 13 illustrates exemplary reconstructed images 1300, 1302, 1304, 1306, 1308, and 1310 of three vertically stacked 7.5×7.5×7.5 $cm^3$ tungsten blocks (side view) with separation of 15 cm in accordance with some embodiments described herein. Data were acquired on a muon tomography system. Images were reconstructed using a PoCA program. Acquisition time was 300 seconds (top row images) that led to the same total muons used in the simulation studies. Doubling the acquisition time to 600 seconds (bottom row images 1306, 1308, and 1310) showed significantly improved image quality. The images clearly demonstrated the decreased (visually diminished) separation between the blocks using the small zenith angle subset (left images 1300 and 1306), but significantly improved separation between the blocks using the large zenith angle subset (middle images 1302 and 1308). The separation between the tungsten blocks in the overall image (this is the conventional reconstruction setting) 1304 and 1310 was better than the small zenith angle subset but significantly poorer than the large zenith angle subset. The above results are consistent with the corresponding simulation results.

Figure 14:
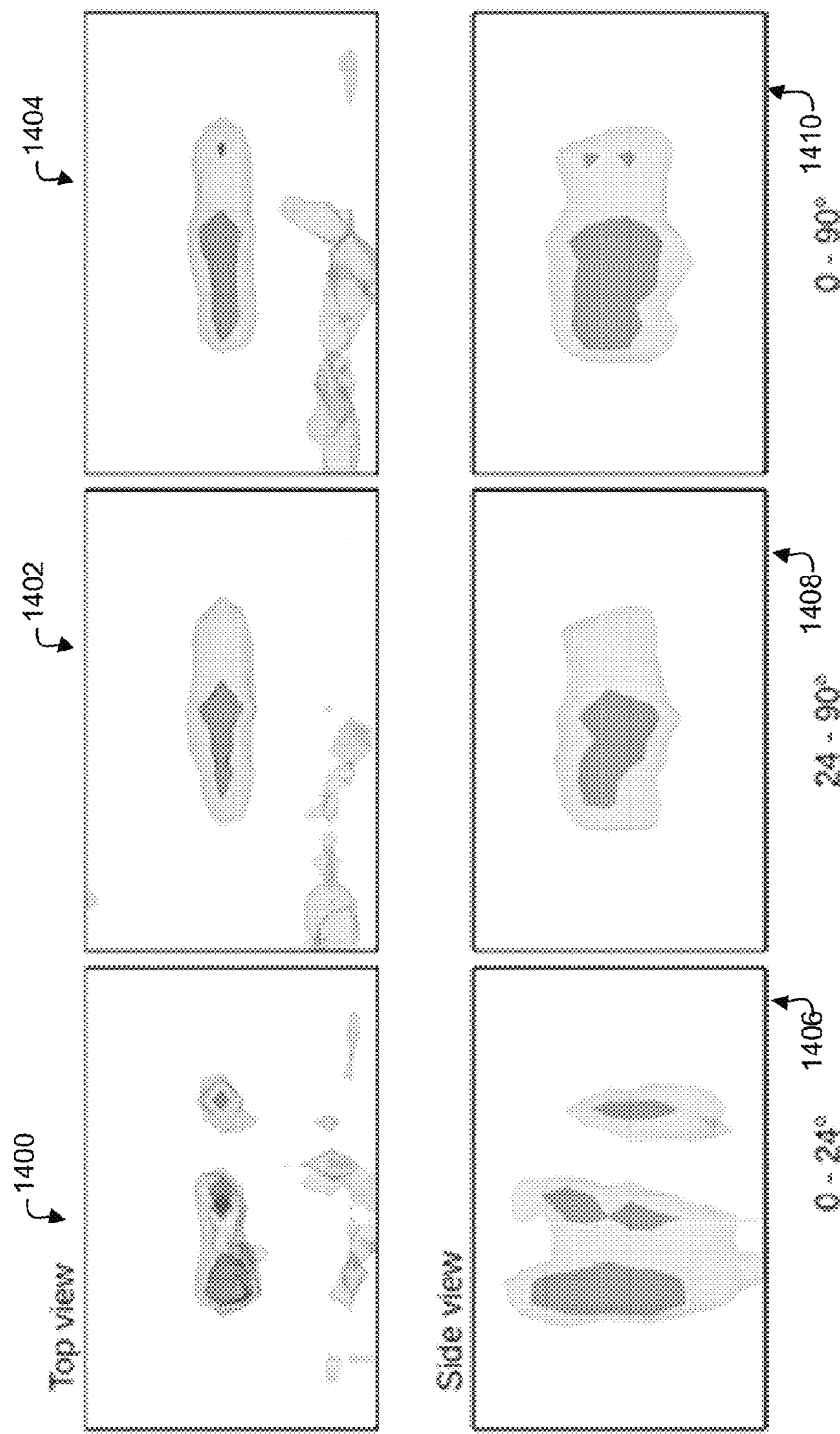
FIG. 14 illustrates the reconstructed images of three side stacked tungsten blocks with separation of 5 cm in accordance with some embodiments of the disclosed technology.

FIG. 14 illustrates exemplary reconstructed images 1400, 1402, 1404, 1406, 1408, and 1410 of three side stacked tungsten blocks with separation of 5 cm in accordance with some embodiments described herein. Data were acquired on a muon tomography system in 600 seconds. The small zenith angle subset images (left images 1400 and 1406) clearly showed the separations between the blocks, but the large zenith angle subset images (middle images 1402 and 1408) and the overall images (right images 1404 and 1410) did not show any separation. In the side view (bottom row 1406, 1408, and 1410), however, the images showed better vertical resolution recovery using the large zenith angle subset than the small zenith angle subset and the overall data.

Figure 15:
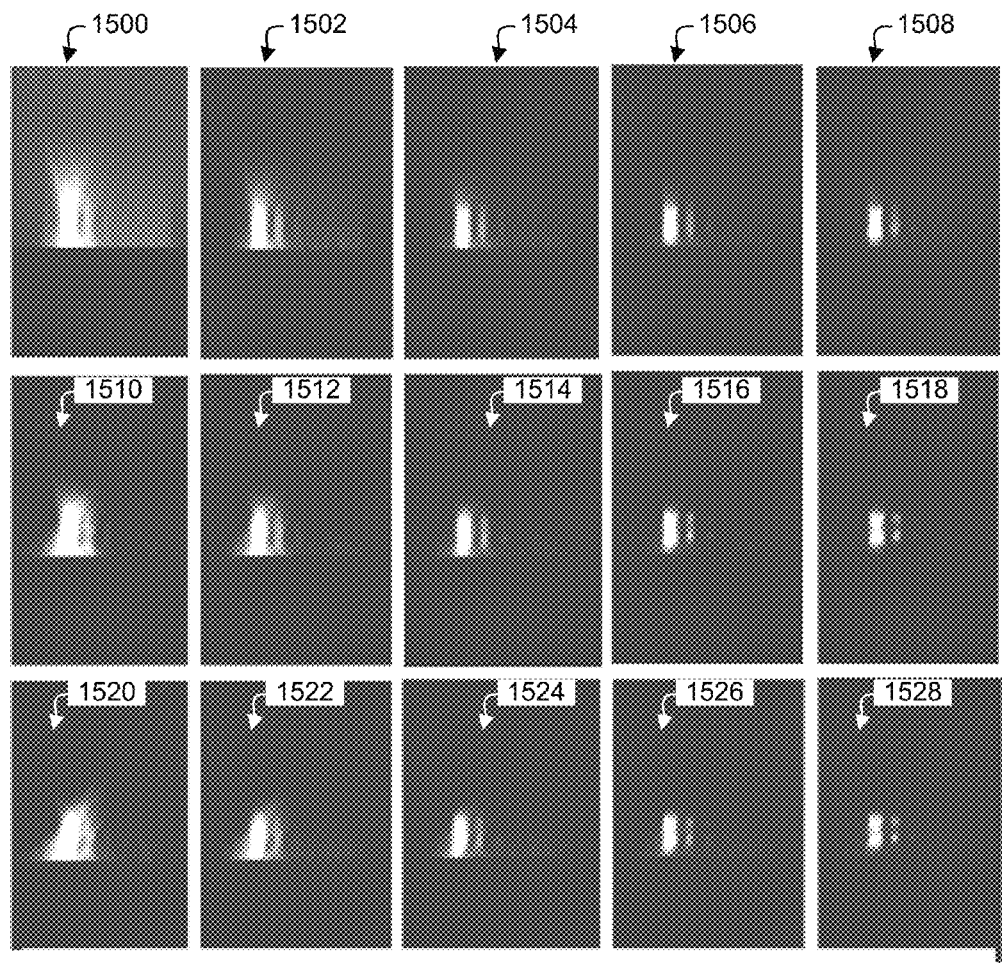
FIG. 15 illustrates the vertical resolution recovery with successive iterations (1 to 5 from left to right) using the accelerated MLEM technique for subsets with different zenith angle ranges in accordance with some embodiments of the disclosed technology.

FIG. 15 illustrates exemplary vertical resolution recovery with successive iterations (1 to 5 from left to right) using the accelerated MLEM technique for subsets with different zenith angle ranges in accordance with some embodiments described herein. The images from top to bottom are: 0°-24° subset (1500, 1502, 1504, 1506, and 1508), 24°-90° subset (1510, 1512, 1514, 1516, and 1518), and the overall dataset 0°-90° (1520, 1522, 1524, 1526, and 1528). These images progressively visualize the impact of muon angles on the resolution recovery, wherein vertical separation of the tungsten blocks were recovered the best with the large zenith angle subset, followed by the overall data, and finally the small zenith angle subset.

Results in the first set of the simulations (i.e., FIGS. 5 and 6) in which the tungsten blocks are effectively isolated from each other, the overall image quality and the block definition are all very good with the relatively small differences between the images of different subsets. When the blocks get closer to each other in the second and third sets of simulations (i.e., FIGS. 7, 9 and 11), however, the effect of limited angular distribution of the incident cosmic ray muons becomes evident. Hence, the present disclosure has used subsets of muon scattering data to systematically illustrate how image resolution varies with the detected muon angular distribution, especially by using the progressive resolution recovery in iterative reconstruction as shown in FIG. 15.

In some of the described simulations, two subsets of muon scattering data that have about the same number of muon tracks (e.g., 48.1% vs. 51.9%) are used. To optimize the result of the using angular subset data partition, two competing factors need to be considered: one is the angular range for the targeted resolution direction, and the other is the total muon counts for a given subset. The latter factor is important mainly because the muon flux rate is typically too low (1 muon/min/cm$^2$). For homeland security applications, such as cargo screening scans, scanning time of two minutes will acquire an average of 50 counts on a 5 cm by 5 cm area. As such, an aggressive regrouping of data to smaller angular ranges may lead to high noise in the reconstructed image that can deteriorate the image fidelity for applications such as special nuclear material detection.

Some of the above-described results showed that the vertical gap of 15 cm was not recovered by the small zenith angle subset of data, but was significantly recovered by the large zenith angle subset of data. This implies that by increasing the angular range of the data, better vertical resolution in reconstructed muon images can be achieved. One way to increase the angular range of the data is to use more side detectors positioned on one or more sides perpendicular to the detector plane of the muon tomography system to detect more horizontally propagation muons. It is expected that with more horizontally propagation muons (i.e., large zenith angle muons) detected, the vertical resolution can be further improved.

Combining the simulations results of both vertically and horizontally stacked tungsten blocks, the results showed that using the small zenith angle subset, a vertical gap of 15 cm was not recovered but horizontal gaps of 15 cm and 10 cm were clearly recovered. This indicates that by rotating the object (e.g., the tungsten blocks) about an axis in the horizontal plane by an angle no more than 90°, smaller vertical gaps between the blocks can be resolved. Note that rotating the objects around a horizontal axis changes the object orientation relative to the cosmic ray muon angular distribution, effectively increasing the detected muon angular range without adding side detectors. While rotating the object may increase the total scan time, depending upon the amount of rotation, the increased angular range of the detected muons can lead to more accurate and better quality of reconstructed images.

Figure 16:
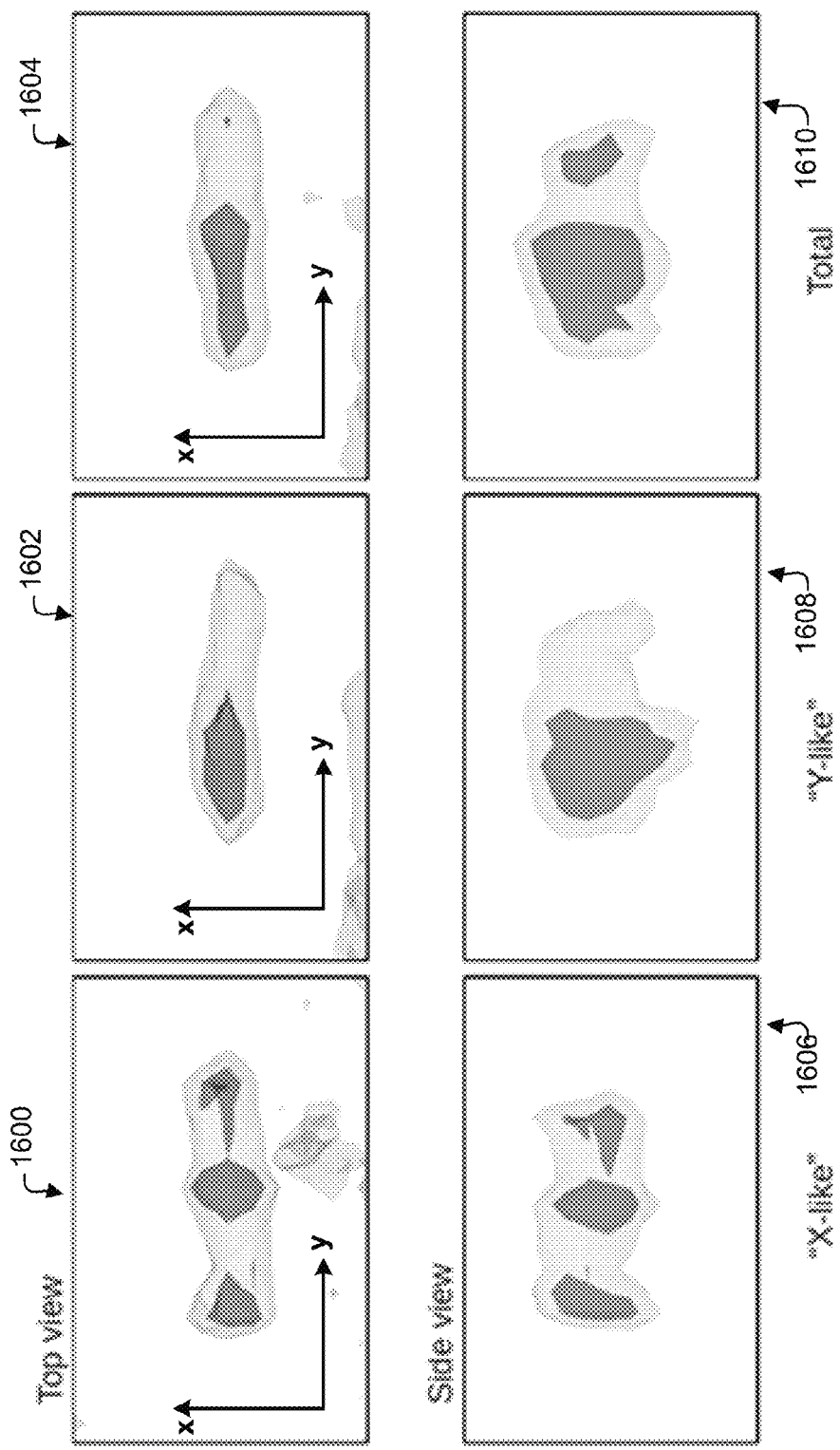
FIG. 16 illustrates reconstructed images of three tungsten blocks arranged with 5 cm separation along the y-direction in the horizontal plane based on an alternative partitioning of the measured muon data in accordance with some embodiments of the disclosed technology.

The above discussion focuses on the use of the zenith angle to partition the data. Based on the applications, however, data can also be partitioned into subsets in manners other than the zenith angle to allow for improving resolution in desired directions. FIG. 16 illustrates exemplary reconstructed images of three tungsten blocks arranged with 5 cm separation along the y-direction in the horizontal plane based on an alternative partitioning of the measured muon data in accordance with some embodiments described herein. Data were acquired on an exemplary muon tomography system in 600 seconds.

The data partition method used in FIG. 16 aims at resolving separations in the x and y directions in the horizontal plane parallel to the detector surfaces. Muon tracks in the measured data are partitioned based on whether their trajectory is closer to being parallel with x-direction (referred to as "X-like" subset) or closer to being parallel to y-direction (referred to as "Y-like" subset). As can be seen in FIG. 16, the "X-like" subset images (left ones) 1600 and 1606 clearly show the separations of the blocks, while the "Y-like" subset image (middle) 1602 and 1608 and the overall dataset images (right) 1604 and 1610 show obvious blurring in the y-direction because the blocks are positioned along the y-direction. Also, the side view image of the "X-like" subset (bottom-left) 1606 shows much better vertical resolution than the small angle subset of the zenith angle partitioned data (i.e., the bottom left image 1406 in FIG. 14), indicating the "X-like" subset achieves good resolution in both y-direction and the vertical direction. This result is consistent with the results from using zenith angle subsets because the "X-like" data includes muons of all zenith angles.

Figure 17:
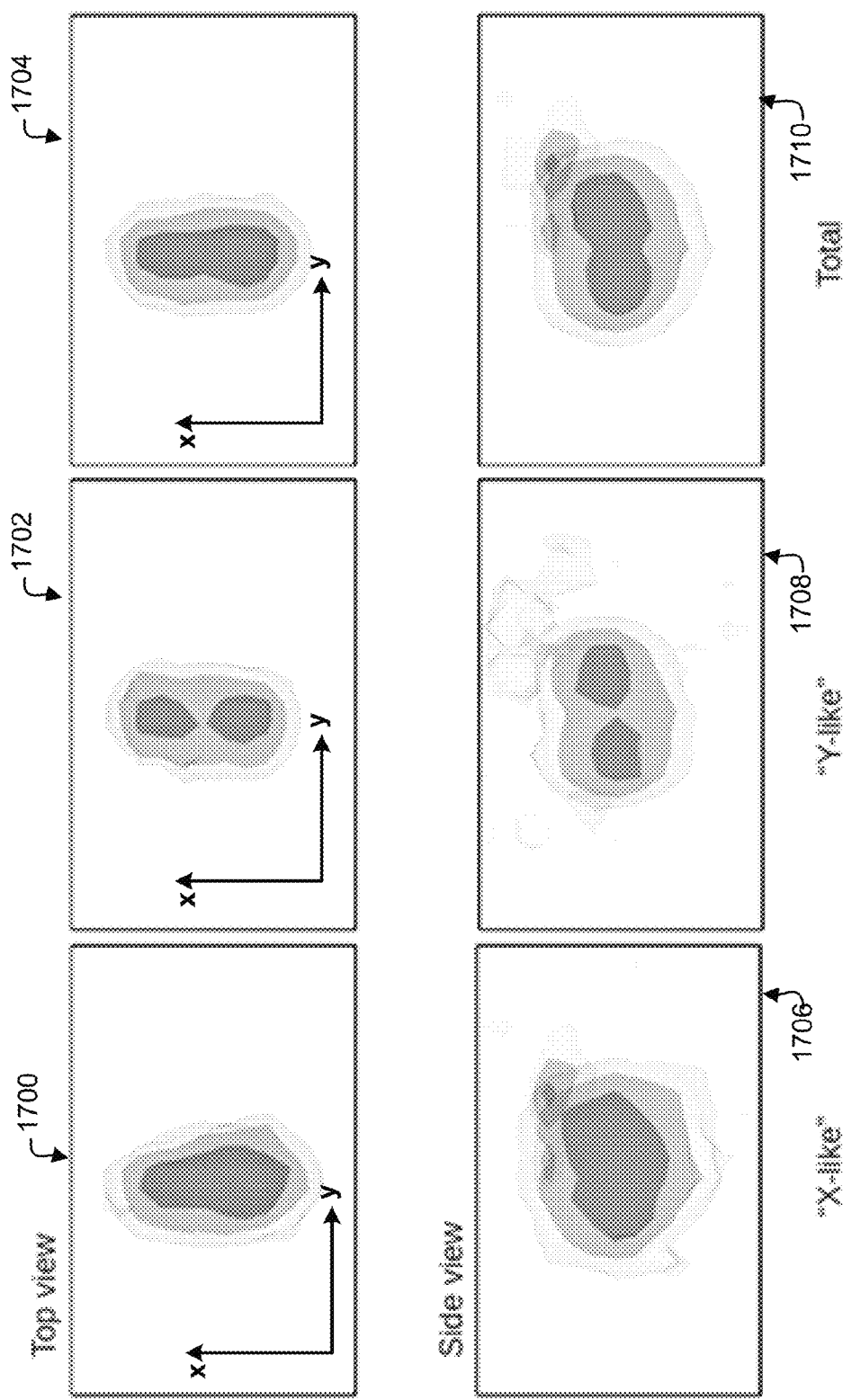
FIG. 17 illustrates reconstructed images of two tungsten blocks arranged with 5 cm separation along the x-direction based on the X-Y partitioning of the measured muon data in accordance with some embodiments of the disclosed technology.

FIG. 17 illustrates exemplary reconstructed images 1700, 1702, 1704, 1706, 1708, and 1710 of two tungsten blocks arranged with 5 cm separation along the x-direction based on the X-Y partitioning of the measured muon data in accordance with some embodiments described herein. Data for FIG. 17 were acquired on a separate muon tomography system with similar geometry to the one used for FIG. 16 but smaller in size, so that both data sets have a similar angular distribution of incident muons. As can be seen in FIG. 17, the images of the "Y-like" subset (left) 1700 and 1706 clearly show the separations, while the "X-like" subset images (middle) 1702 and 1708 and the overall data images (right) 1704 and 1710 show obvious blurring in the x-direction.

Figure 18:
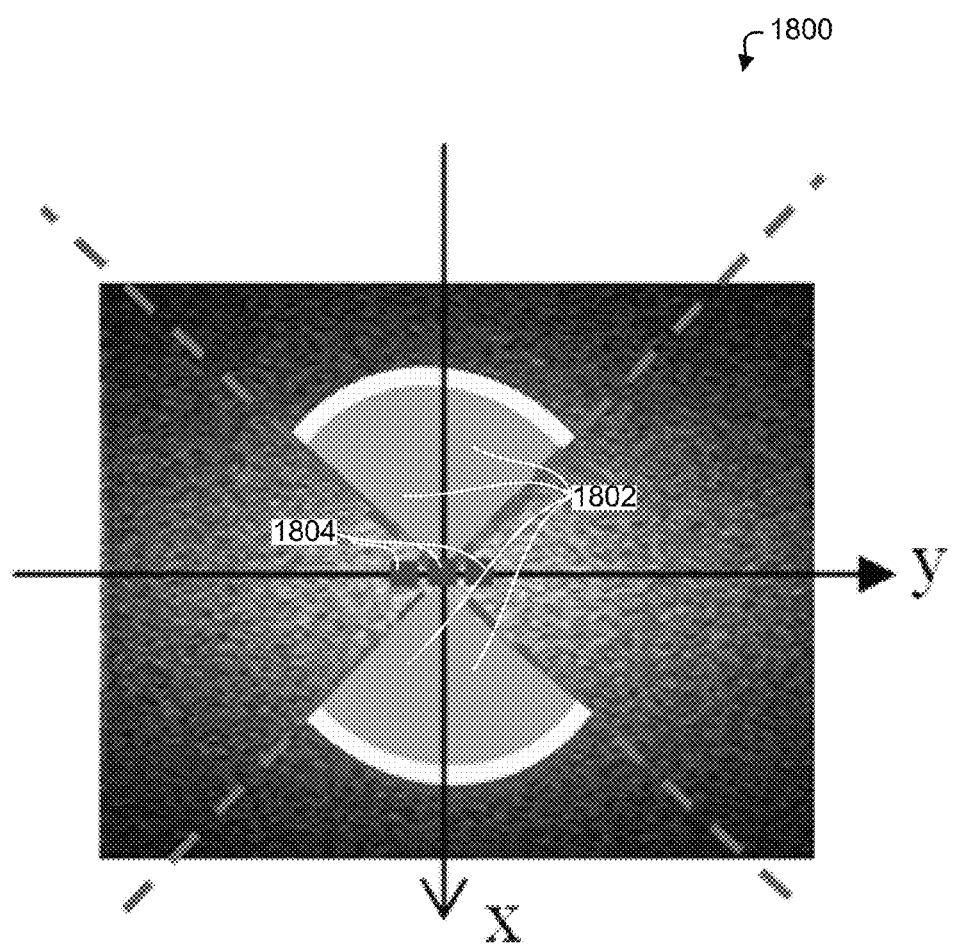
FIG. 18 illustrates that the "X-like" and "Y-like" partitions of the data is equivalent to the regrouping of muons based on the azimuthal angle in accordance with some embodiments of the disclosed technology.

FIG. 18 is a data chart 1800 showing that the "X-like" and "Y-like" partitions of the data is equivalent to the grouping of muons based on the azimuthal angle in accordance with some embodiments of the disclosed technology. In FIG. 18, the background image is the projection image in FIG. 2B. More specifically, the "X-like" subset of data is the muons with azimuthal angle shown in green 1802. The rest of the muons belong to the "Y-like" subset of data. The three squares 1804 show the positions of the three tungsten blocks along the y direction in the measurement. The squares 1804 are not drawn proportional to the physical size of the blocks relative to the detector for illustration purpose. The "X-like" muons can reconstruct the gaps along y direction better than the "Y-like" muons because the "X-like" muons have a larger perpendicular component to the y-direction than the "Y-like" muons. In the embodiment of FIG. 15, the x-direction is along the small dimension of the detector and the "X-like" muons account for 46% of the total muons. The y-direction is along the large dimension of the detector, so the remaining 54% of muons are in the "Y-like" partition.

Figure 19:
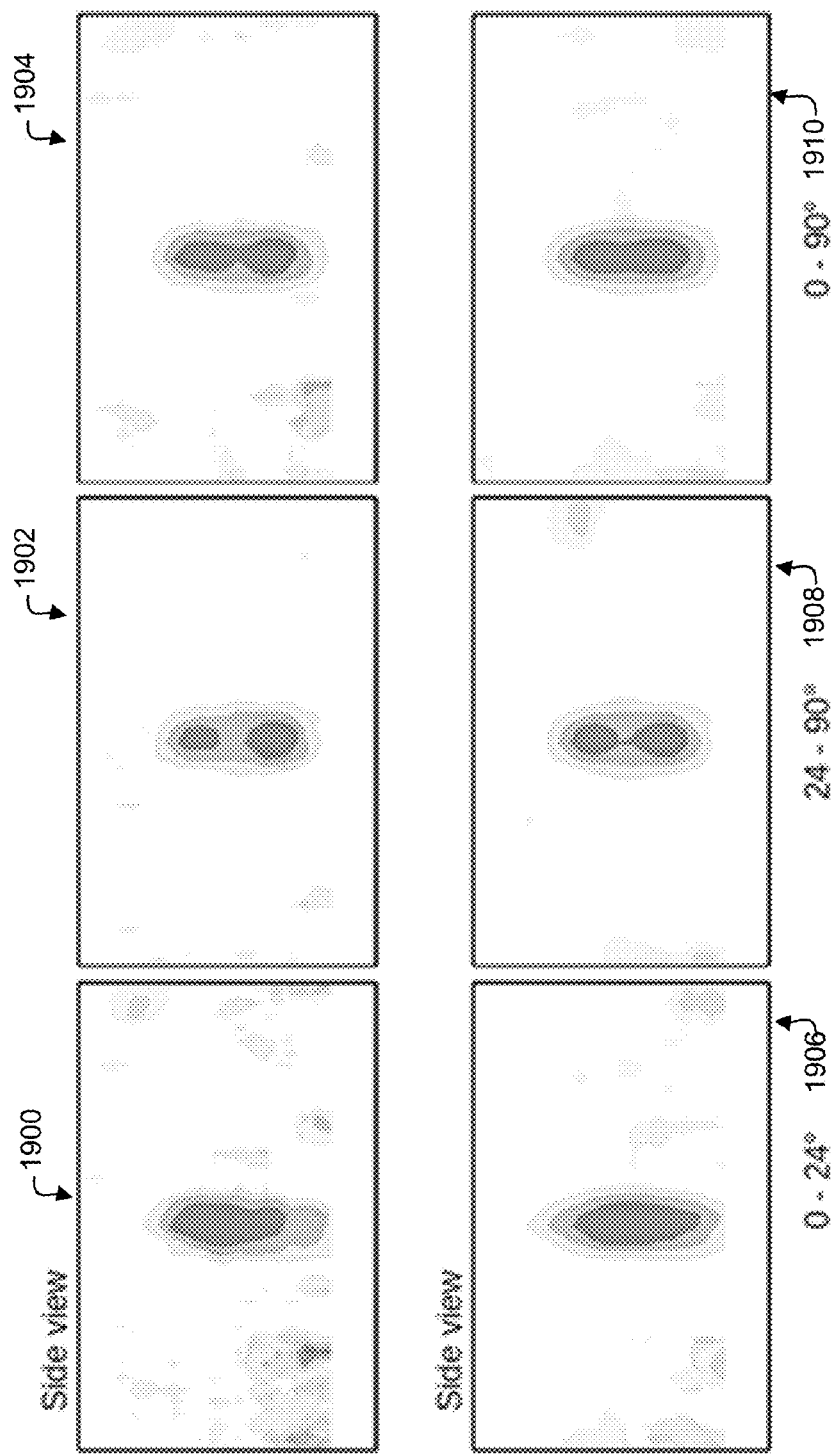
FIG. 19 illustrates reconstructed images of two tungsten blocks arranged with 10 cm vertical separation in accordance with some embodiments of the disclosed technology.

Further analysis shows that simply increasing the quantity of data (extending scan time) may not be sufficient to achieve optimal resolution, particularly in the vertical direction. FIG. 19 illustrates exemplary reconstructed images 1900, 1902, 1904, 1906, 1908, and 1910 of two tungsten blocks arranged with 10 cm vertical separation in accordance with some embodiments of the disclosed technology. Data were acquired on a smaller muon tomography system in 600 second (top row images 1900, 1902, and 1904) and 3600 seconds (bottom row images 1906, 1908, and 1910). While it is evident from FIG. 19 that the overall image quality improves as we increase scan time to obtain additional data (i.e., reduced background noise and smoother reconstructed objects in images), the problem of poor vertical resolution persists because the additional data is still subject to the zenith angle limitation of incident muons. In fact, the vertical resolution using the high zenith angle subset of data at 600 seconds (top middle 1902) is better than the resolution using the overall data at 3600 seconds (bottom right 1910). The result of FIG. 19 demonstrates the necessity of reconstructing using optimized subsets of the available data in order to achieve maximal image resolution.

In some implementations, to achieve an optimal resolution of special nuclear materials, one can regroup the muon data into an optimal collection of subsets: one subset with small zenith angle, one subset with large zenith angle, and a number of additional subsets determined by an azimuthal partitioning, such as the 90° partitioning used for "X-like" and "Y-like" subsets, or possibly even smaller angles such as 30° or 45°. Note that different subsets can overlap, meaning that a single track can be grouped into multiple subsets. In some implementations, based on the original reconstructed images, the system can decide if the data should be repartitioned into custom subsets based on the identified object orientation in the reconstructed images.

Figure 20:
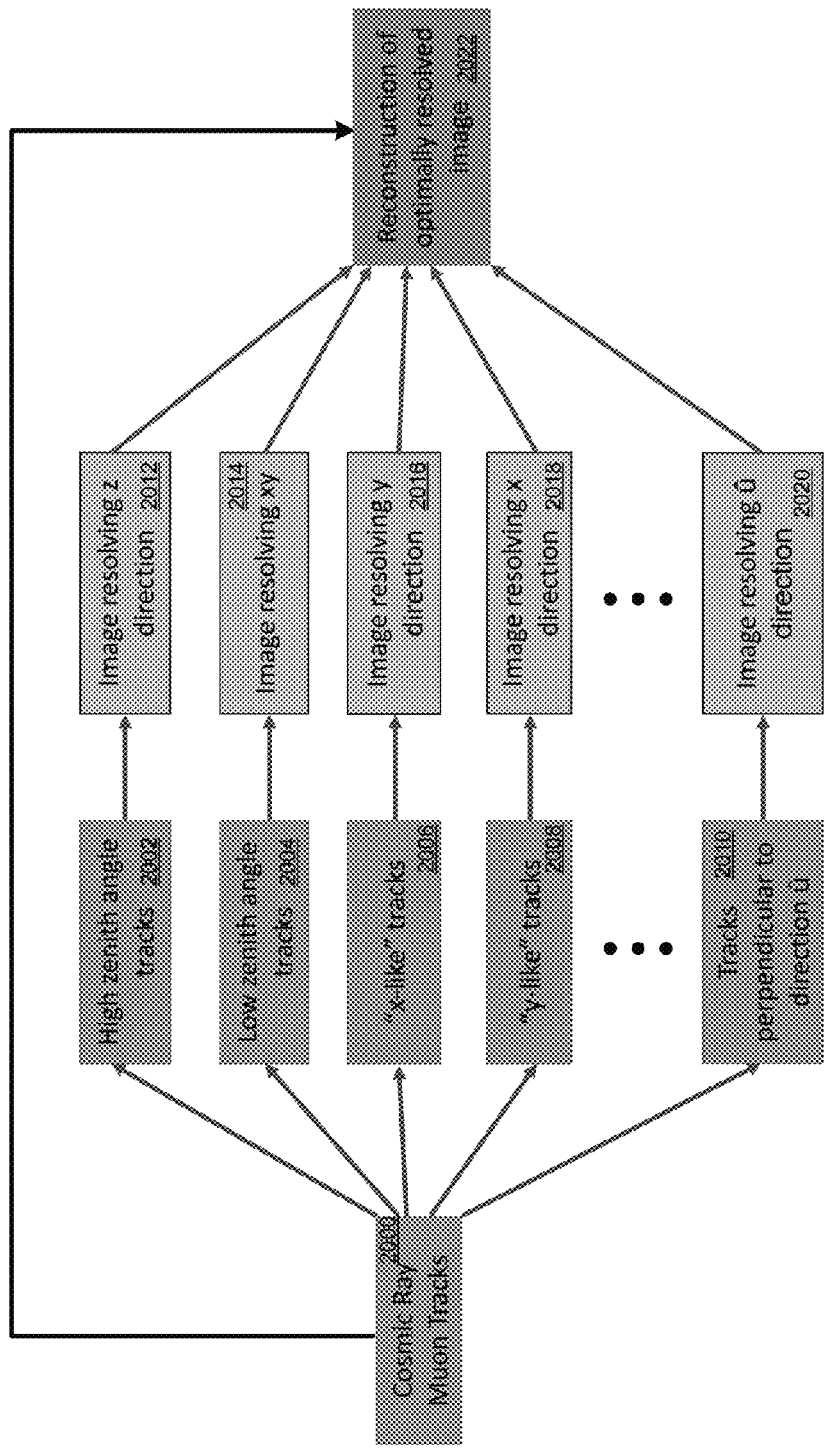
FIG. 20 illustrates a block diagram of regrouping raw cosmic ray muon track data into a collection of subsets and using the subsets of data to generate multiple images in accordance with some embodiments of the disclosed technology.

FIG. 20 illustrates a block diagram of grouping raw cosmic ray muon track data into a collection of subsets and using the subsets of data to generate multiple images in accordance with some embodiments described herein. As can be seen in FIG. 20, a subset of high zenith angle tracks (2002) is used to generate an image having a high resolution in the z-direction (2012); a subset of low zenith angle tracks (2004) is used to generate an image having a high resolution in the xy-plane (2014); a subset of X-like tracks (2006) is used to generate an image having a high resolution in the y-direction (2016); a subset of Y-like tracks (2008) is used to generate an image having a high resolutions in the x-direction (2018); a subset of muon tracks perpendicular to a specific direction û (2010) is used to generate an image having a high resolutions in the û-direction (2020); and so on. The images from the various subsets 2002, 2004, 2006, 2008, . . . , 2010 are combined with an image from the entire set of raw cosmic ray muon tracks (2000) to generate a resultant reconstructed image 2020.

Figure 21:
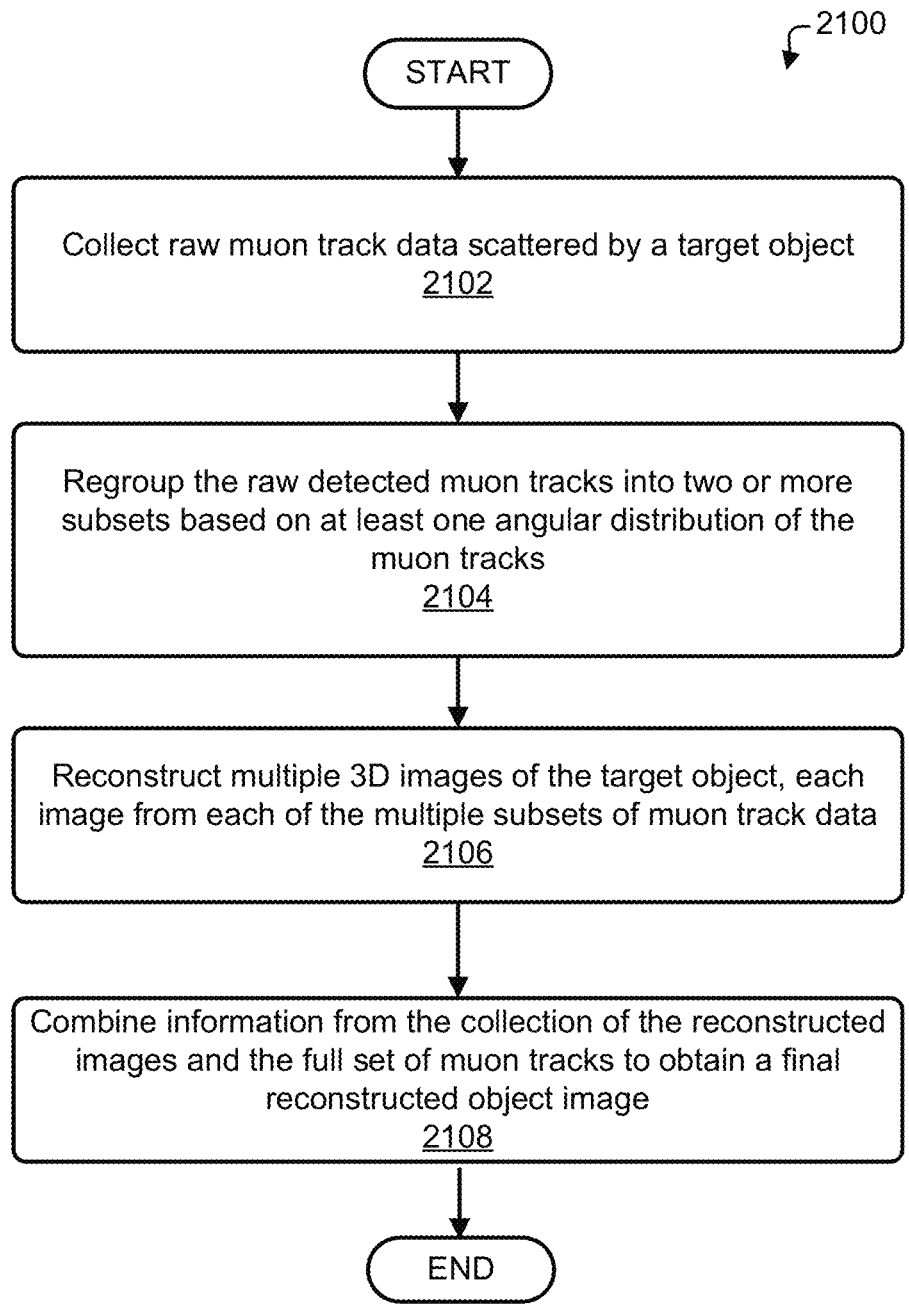
FIG. 21 presents a flowchart illustrating a process of reconstructing tomographic image based on raw cosmic ray muon track data in accordance with some embodiments of the disclosed technology
Figure 22A:
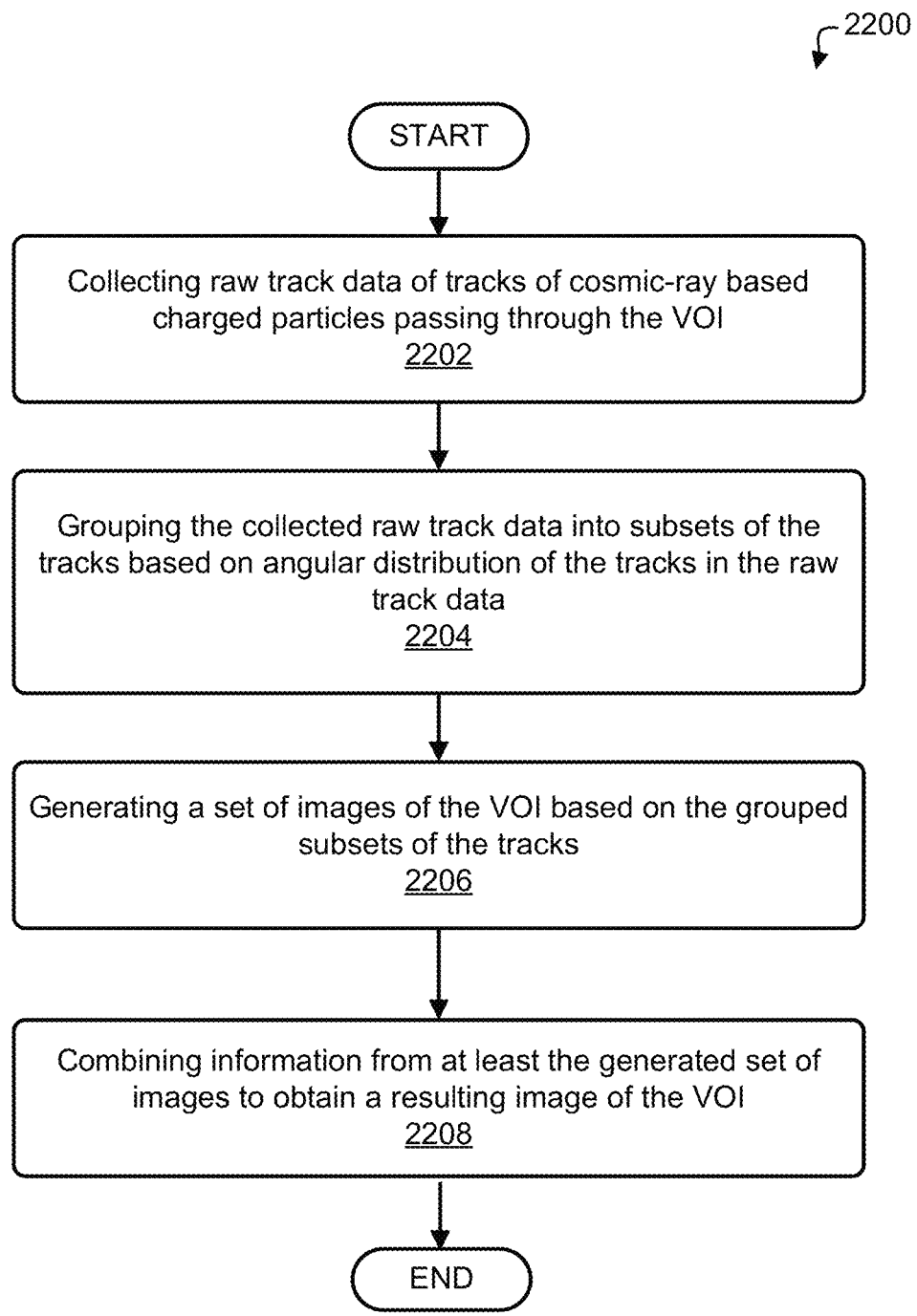
FIGS. 22A, 22B, 22C, 22D, 22E, 22F, 22G, 22H, and 22I are process flow diagrams of a process 2200 for generating charged particle tomography images for a volume of interest (VOI) by a charged particle tomography system.
Figure 22B:
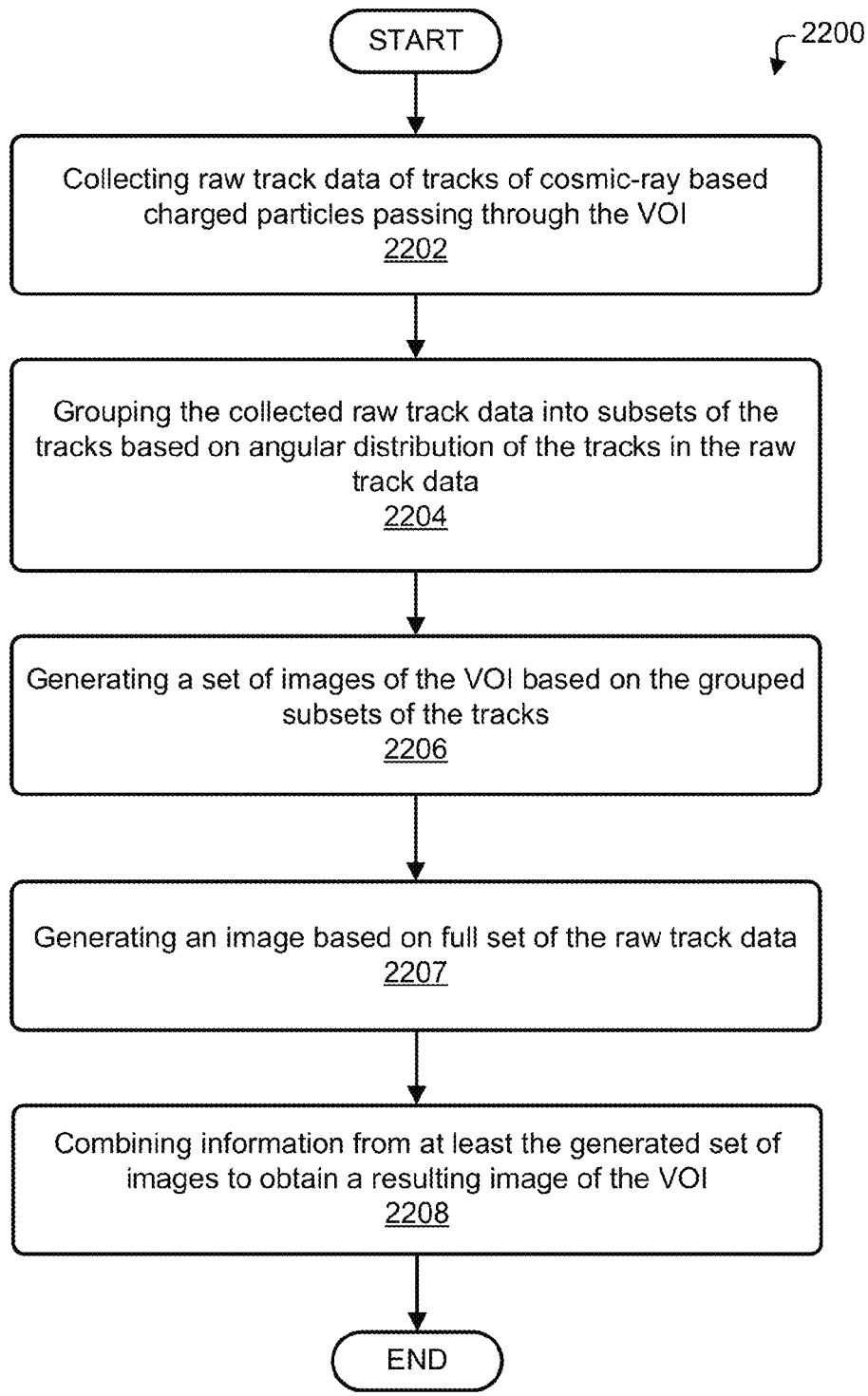
Figure 22C:
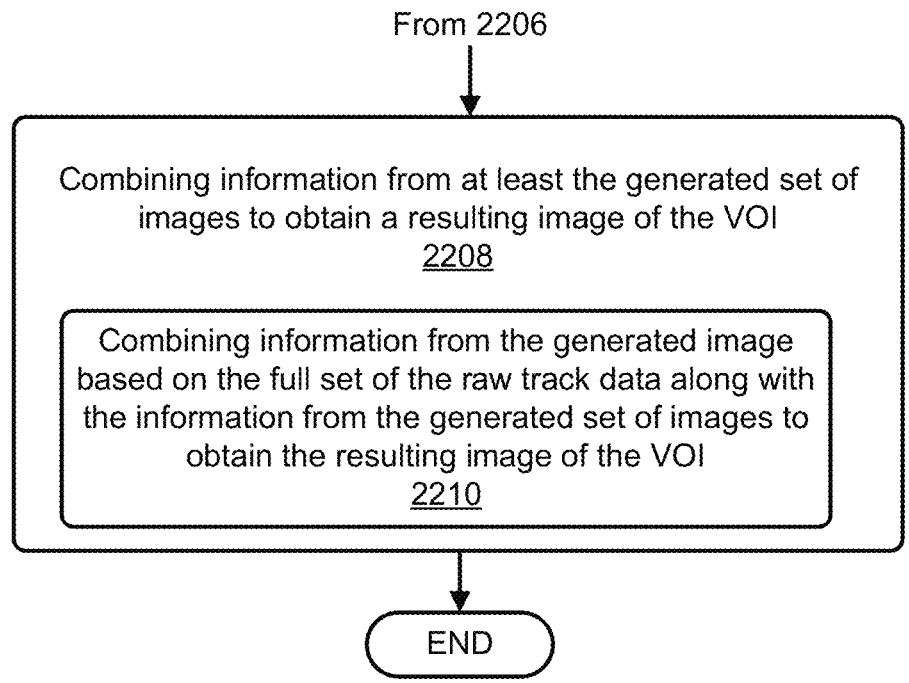
Figure 22D:
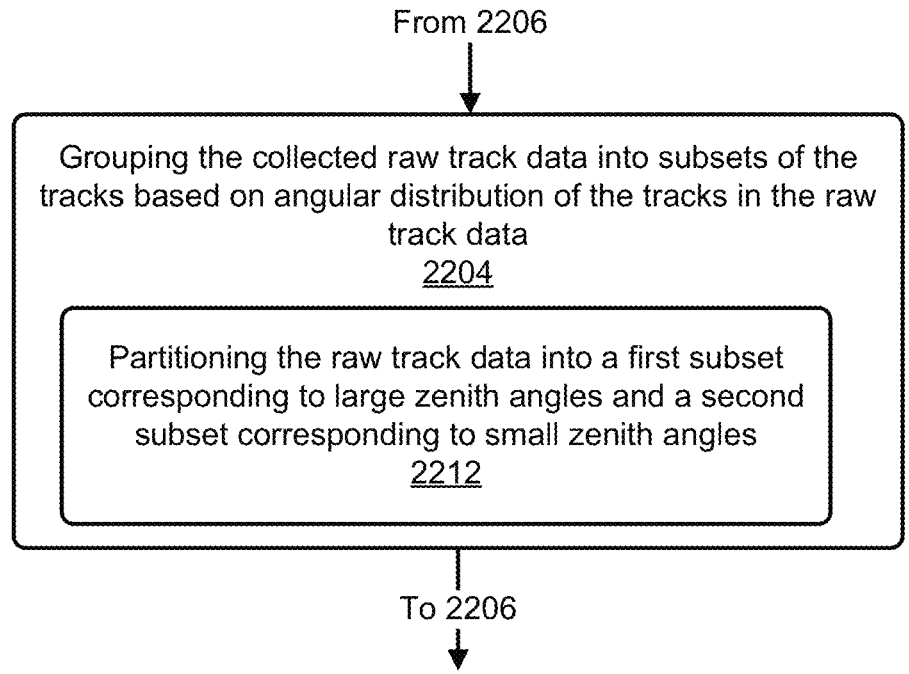
Figure 22E:
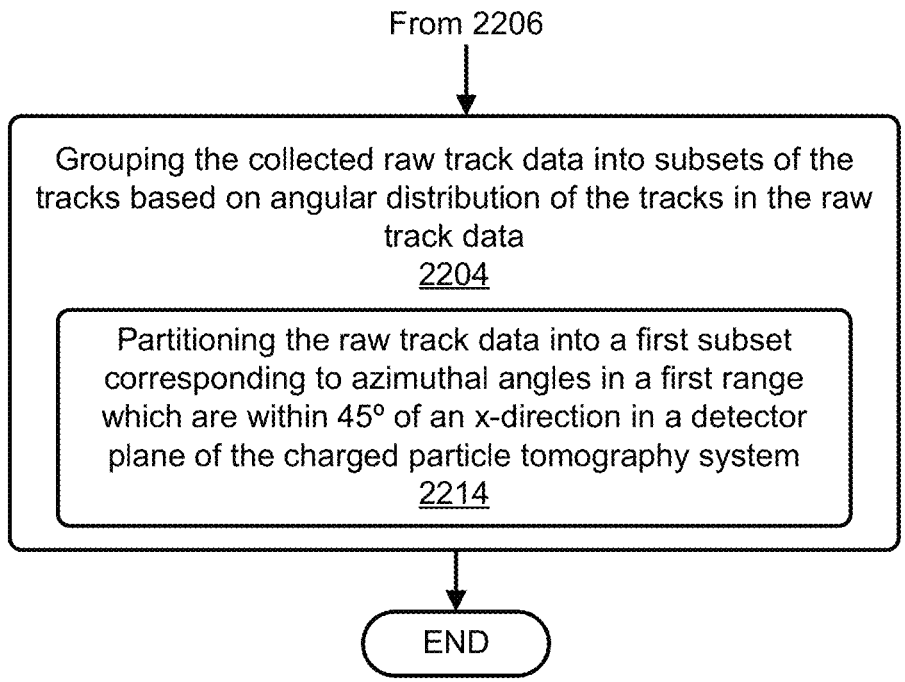
Figure 22F:
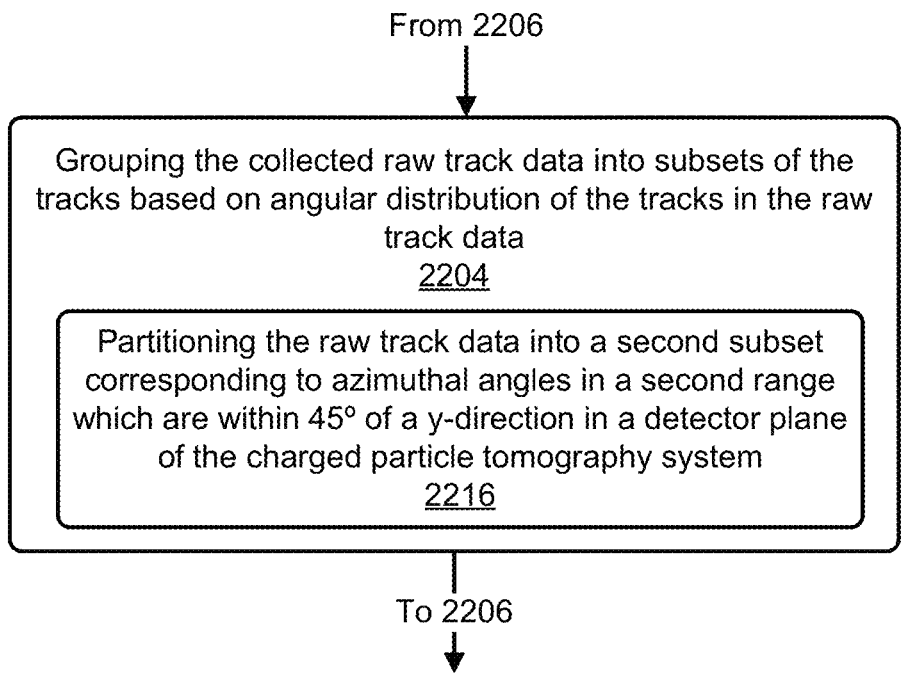
Figure 22G:
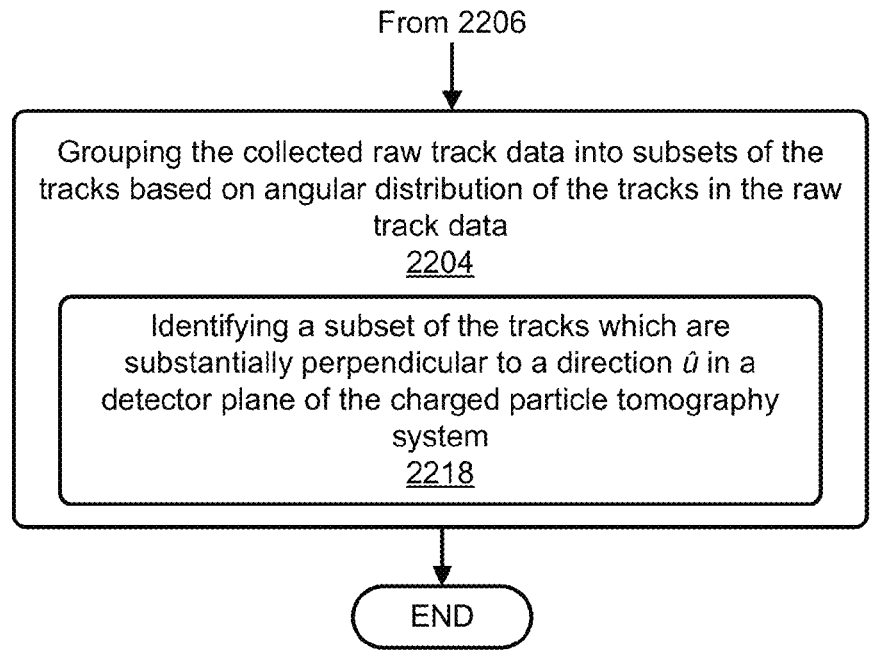
Figure 22H:
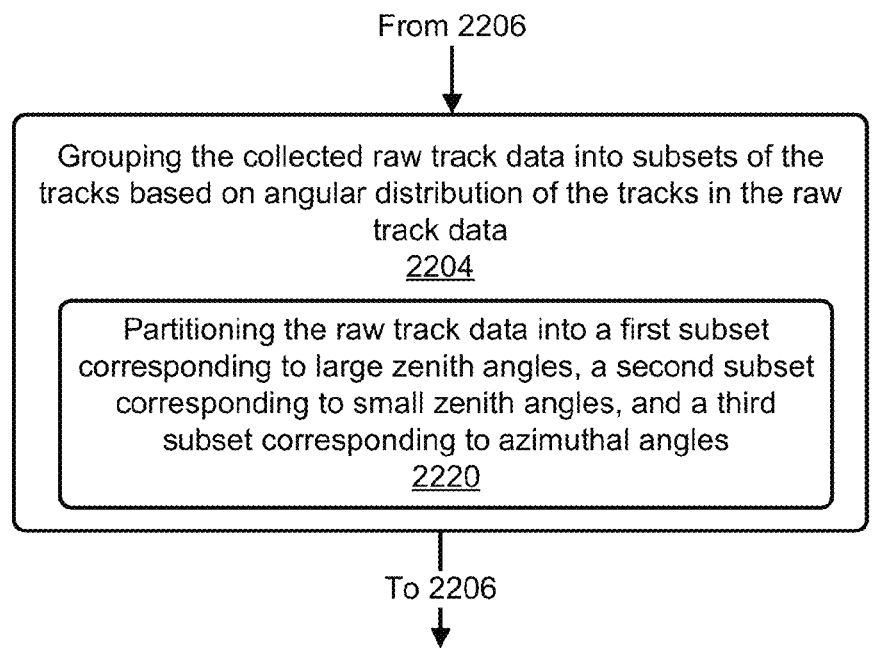
Figure 22I:
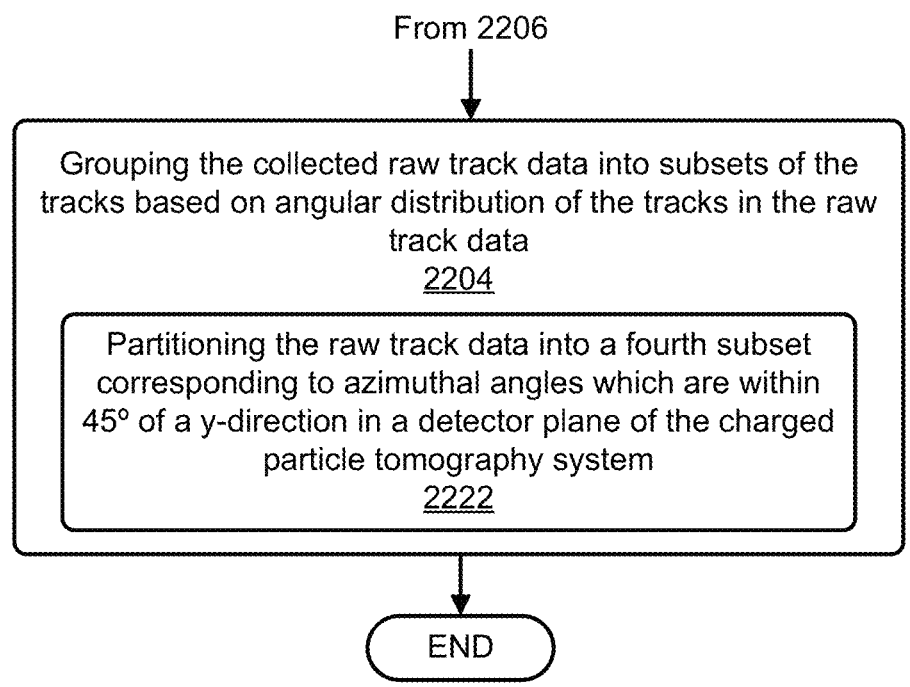
Figure 23A:
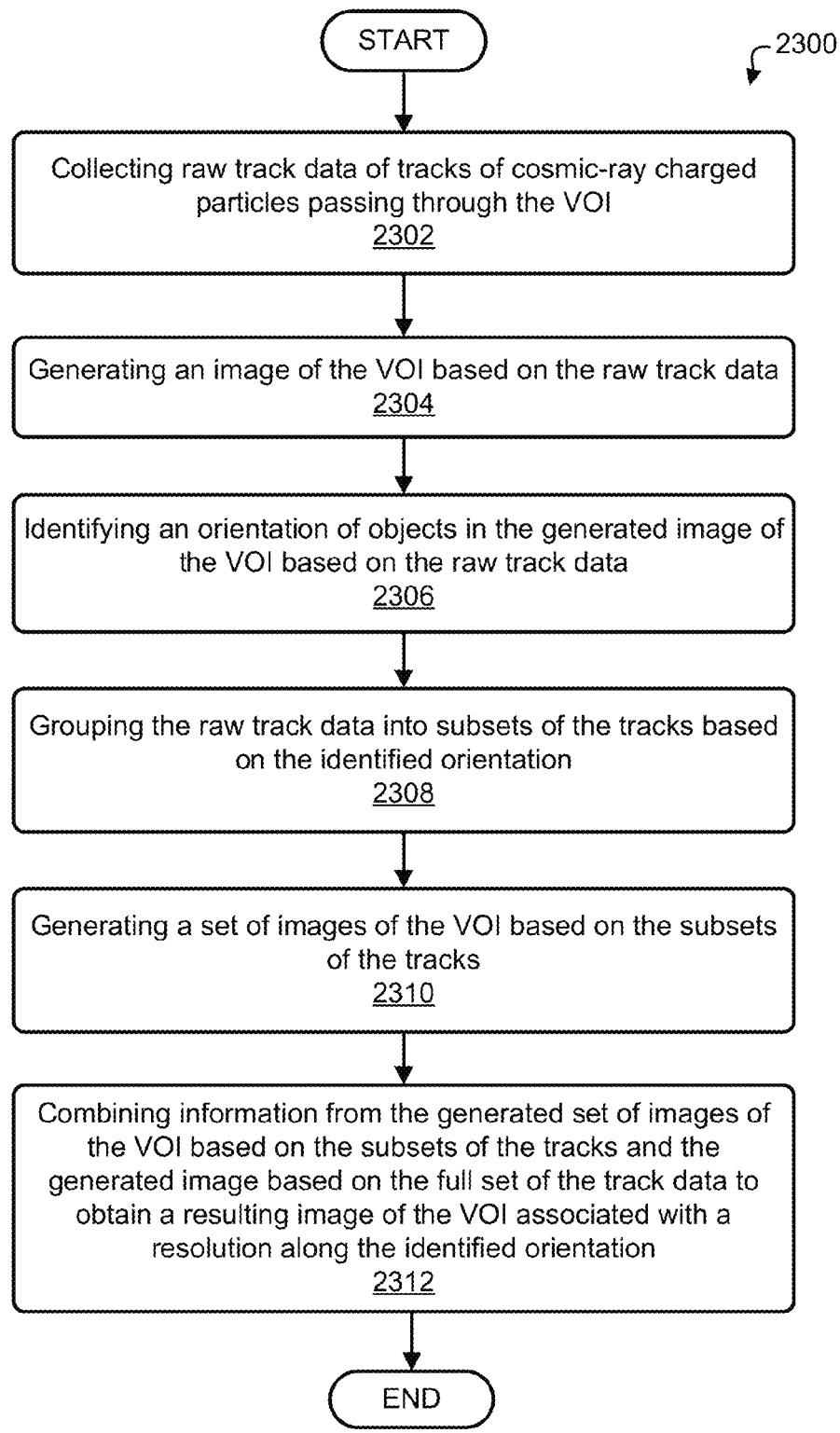
FIGS. 23A, 23B, 23C, 23D, and 23E are process flow diagrams of a process for generating charged particle tomography images for a volume of interest (VOI) by a charged particle tomography system.
Figure 23B:
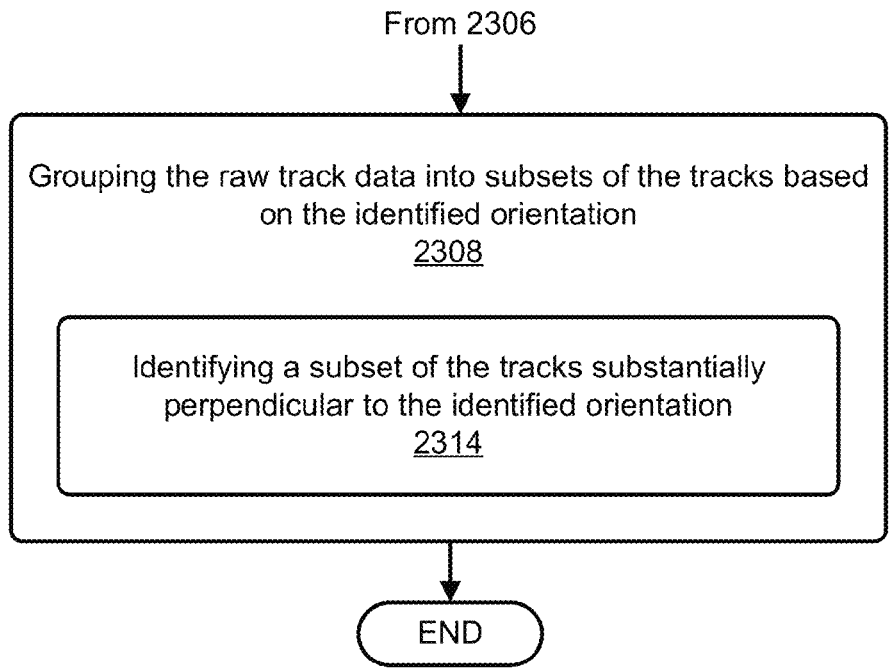
Figure 23C:
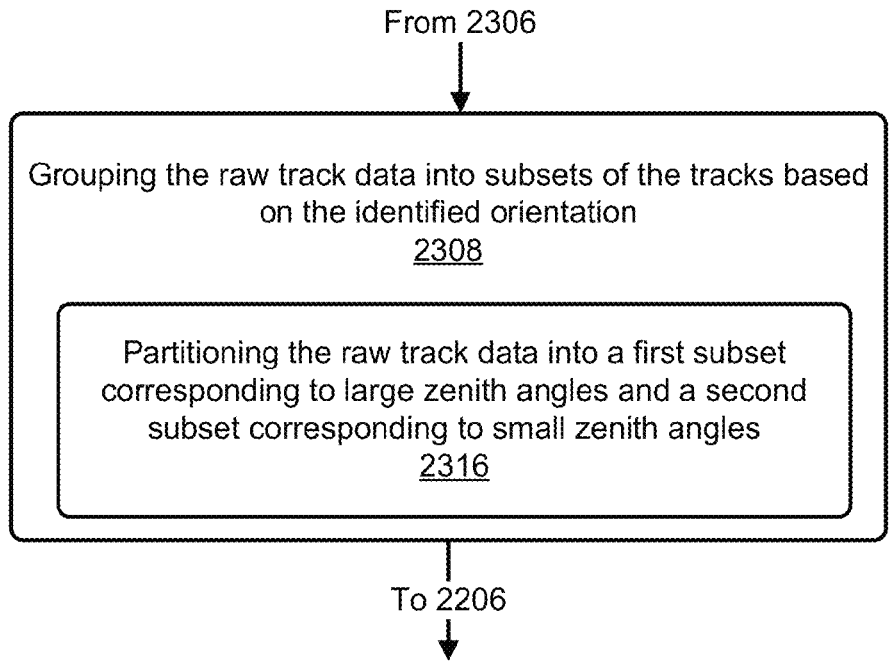
Figure 23D:
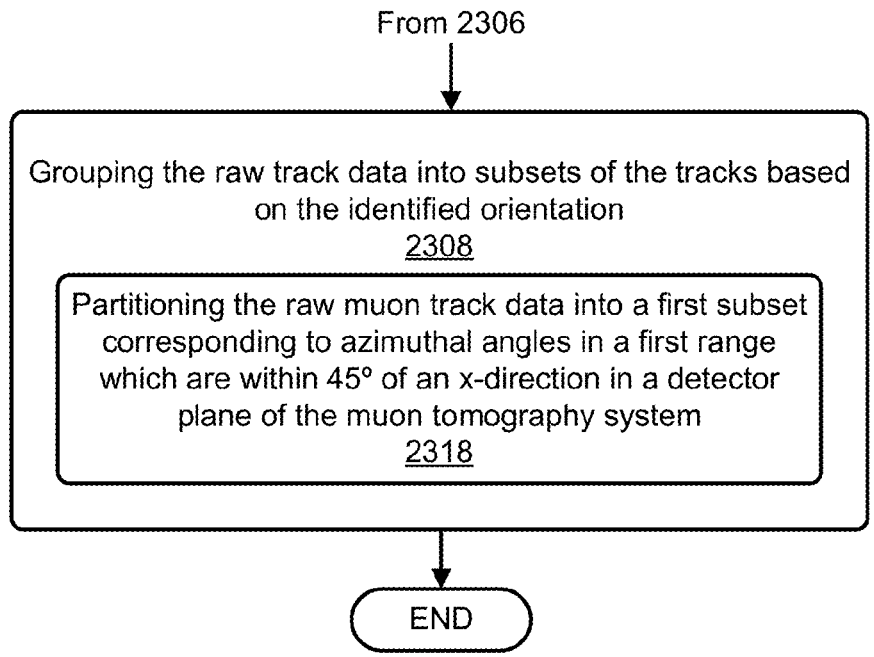
Figure 23E:
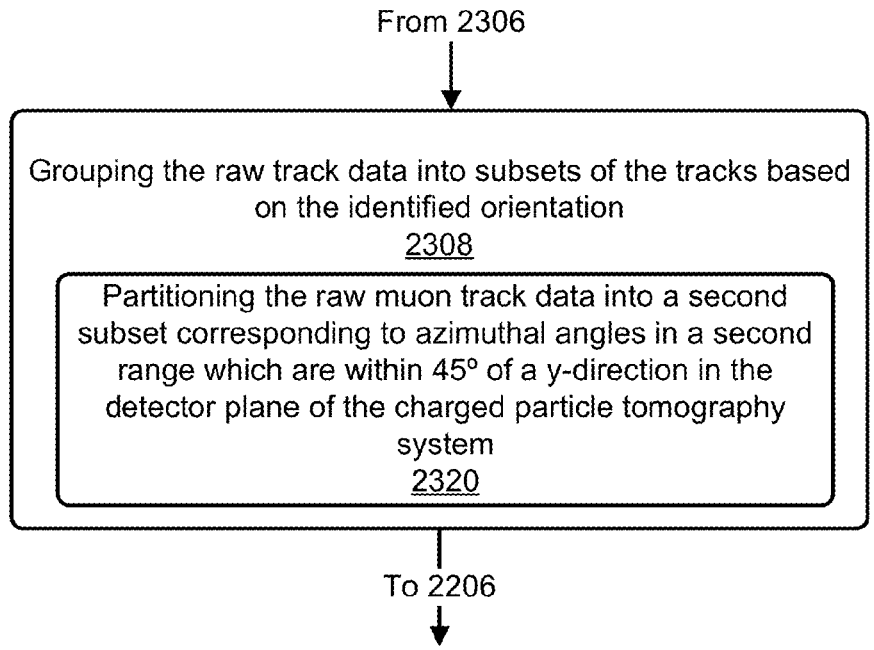

FIG. 21 presents a flowchart illustrating a process 2100 of reconstructing tomographic image based on raw cosmic ray muon track data in accordance with some embodiments described herein. The process includes collecting raw muon track data scattered by a target object (2102). The raw detected muon tracks are grouped into two or more subsets based on at least one angular distribution of the muon tracks (2104). For example, the process can create two subsets based on zenith angle distributions: one subset with high zenith angle tracks and the other subset with low zenith angle tracks. The process can also create two subsets based on azimuthal angle distributions: one subset with X-like tracks and the other subset with Y-like tracks. The process can include creating four subsets based on both zenith and azimuthal angle distributions as listed above. The process can include creating three subsets: two subset based on zenith angle distributions listed above and the third subset including muon tracks perpendicular to a specific direction it for generating an image having a high resolutions in the û-direction. Note that different subsets can overlap, meaning that a single muon track can be grouped into multiple subsets.

The process includes reconstructing multiple 3D images of the target object, each image from each of the multiple subsets of muon track data (2106). For example, if the process has created four subsets based on both zenith and azimuthal angle distributions, four 3D images of the target object are reconstructed from the four subsets. The process can include combining information from the collection of the reconstructed images and the full set of muon tracks to obtain a final reconstructed object image (2108).

Even though the acquired muon data may have limited zenith angle range, the acquired data can be grouped into different limited angle data subsets for optimized image resolution in desired directions. Reconstruction based on the subset data generates multiple images with resolution optimized in different directions. Using such images jointly can improve overall imaging fidelity and the intended applications.

FIGS. 22A, 22B, 22C, 22D, 22E, 22F, 22G, 22H, and 22I are process flow diagrams of a process 2200 for generating charged particle tomography images for a volume of interest (VOI) by a charged particle tomography system. The method includes collecting raw track data of tracks of cosmic-ray based charged particles passing through the VOI (2202). The method includes grouping the collected raw track data into subsets of the tracks based on angular distribution of the tracks in the raw track data (2204). The method includes generating a set of images of the VOI based on the grouped subsets of the tracks (2206). The method includes combining information from at least the generated set of images to obtain a resulting image of the VOI.

The method can be implemented in various ways to include one or more of the following features. For example, the method can include generating an image based on full set of the raw track data (2207). The combining can include combining information from the generated image based on the full set of the raw track data along with the information from the generated set of images to obtain the resulting image of the VOI (2210). Grouping the raw track data into the subsets of the tracks based on the angular distribution can include partitioning the raw track data into a first subset corresponding to large zenith angles and a second subset corresponding to small zenith angles (2212). The first subset of tracks can have a zenith angle range from 0 to X and the second subset of tracks can have a zenith angle range from X to 90°, wherein X is between 20° to 45°. The method can include selecting X so that percentage of the tracks in the first subset and percentage of the tracks in the second subset have a predetermined relationship. The predetermined relationship can include the two percentages being substantially equal to each other. A first image of the set of images based on the first subset of the tracks can be associated with an object resolution in a horizontal direction parallel to a detector plane in the charged particle tomography system. A second reconstructed image based on the second subset of the tracks can be associated with an object resolution in a vertical direction perpendicular to a detector plane in the charged particle tomography system. A third reconstructed image based on the full set of the raw track data can be associated with an object resolution in the horizontal direction which is at a level between the object resolutions in the horizontal direction for the first reconstructed image and the second reconstructed image. The third reconstructed image based on the full set of the raw track data can be associated with an object resolution in the vertical direction at a level between the resolutions in the vertical direction for the first reconstructed image and the second reconstructed image.

The method can be implemented to include one or more of the following features. For example, grouping the raw track data into the subsets of the tracks based on the angular distribution can include partitioning the raw track data into a first subset corresponding to azimuthal angles in a first range which are within 45° of an x-direction in a detector plane of the charged particle tomography system (2214). Grouping the raw track data into the subsets of the tracks based on the angular distribution can include partitioning the raw track data into a second subset corresponding to azimuthal angles in a second range which are within 45° of a y-direction in a detector plane of the charged particle tomography system (2216). A first image of the set of images based on the first subset can be associated with an object resolution in the y-direction. A second reconstructed image of the set of images based on the second subset can be associated with an object resolution in the x-direction. Grouping the raw track data into the subsets of the tracks based on the angular distribution can include identifying a subset of the tracks which are substantially perpendicular to a direction û in a detector plane of the charged particle tomography system (2218). An image based on the identified subset of the tracks substantially perpendicular to the direction û can be associated with an object resolution in the û-direction. Grouping the raw track data into the subsets of the tracks based on the angular distribution can include partitioning the raw track data into a first subset corresponding to large zenith angles, a second subset corresponding to small zenith angles, and a third subset corresponding to azimuthal angles (2220). The large zenith angles, the small zenith angles, and the azimuthal angles for the first, second, and third subsets respectively can be within 45° of an x-direction in a detector plane of the charged particle tomography system. Grouping the raw track data into the subsets of the tracks based on the angular distribution can include partitioning the raw track data into a fourth subset corresponding to azimuthal angles which are within 45° of a y-direction in a detector plane of the charged particle tomography system (2222). At least two of the subsets of the tracks share a common cosmic-ray based charged particle track. The cosmic-ray based charge particles can include muons.

In another aspect, FIGS. 23A, 23B, 23C, 23D, and 23E are process flow diagrams of a process 2300 for generating charged particle tomography images for a volume of interest (VOI) by a charged particle tomography system. The process 2300 includes collecting raw track data of tracks of cosmic-ray charged particles passing through the VOI (2302). The process includes generating an image of the VOI based on the raw track data (2304). The process includes identifying an orientation of objects in the generated image of the VOI based on the raw track data (2306). The process includes grouping the raw track data into subsets of the tracks based on the identified orientation (2308). The process includes generating a set of images of the VOI based on the subsets of the tracks (2310). The process includes combining information from the generated set of images of the VOI based on the subsets of the tracks and the generated image based on the full set of the track data to obtain a resulting image of the VOI associated with a resolution along the identified orientation (2312).

The process can be implemented in various ways to include one or more of the following features. For example, grouping the raw track data into the subsets of the tracks based on the identified orientation can include identifying a subset of the tracks substantially perpendicular to the identified orientation (2314). An image of the set of images based on the identified subset of tracks substantially perpendicular to the identified orientation can be associated with an object resolution in the identified orientation. Grouping the raw track data into the subsets of the tracks can include partitioning the raw track data into a first subset corresponding to large zenith angles and a second subset corresponding to small zenith angles (2316). The first subset of the tracks can have a zenith angle range from 0 to X and the second subset of the tracks can have a zenith angle range from X to 90° with X being between 20° or 45°. A first image based on the first subset of tracks can provide an improvement of an object resolution in a horizontal direction parallel to a detector plane in the charged particle tomography system; and a second image based on the second subset of tracks can provides an improvement of an object resolution in a vertical direction perpendicular to the detector plane in the charged particle tomography system. Grouping the raw track data into the subsets of tracks can include partitioning the raw muon track data into a first subset corresponding to azimuthal angles in a first range which are within 45° of an x-direction in a detector plane of the muon tomography system (2318); and partitioning the raw muon track data into a second subset corresponding to azimuthal angles in a second range which are within 45° of a y-direction in the detector plane of the charged particle tomography system (2320). A first reconstructed image based on the first subset of tracks can be associated with an object resolution in the y-direction. A second reconstructed image based on the second subset of tracks is associated with an object resolution in the x-direction. The cosmic-ray charged particles can include muons.

Figure 24A:
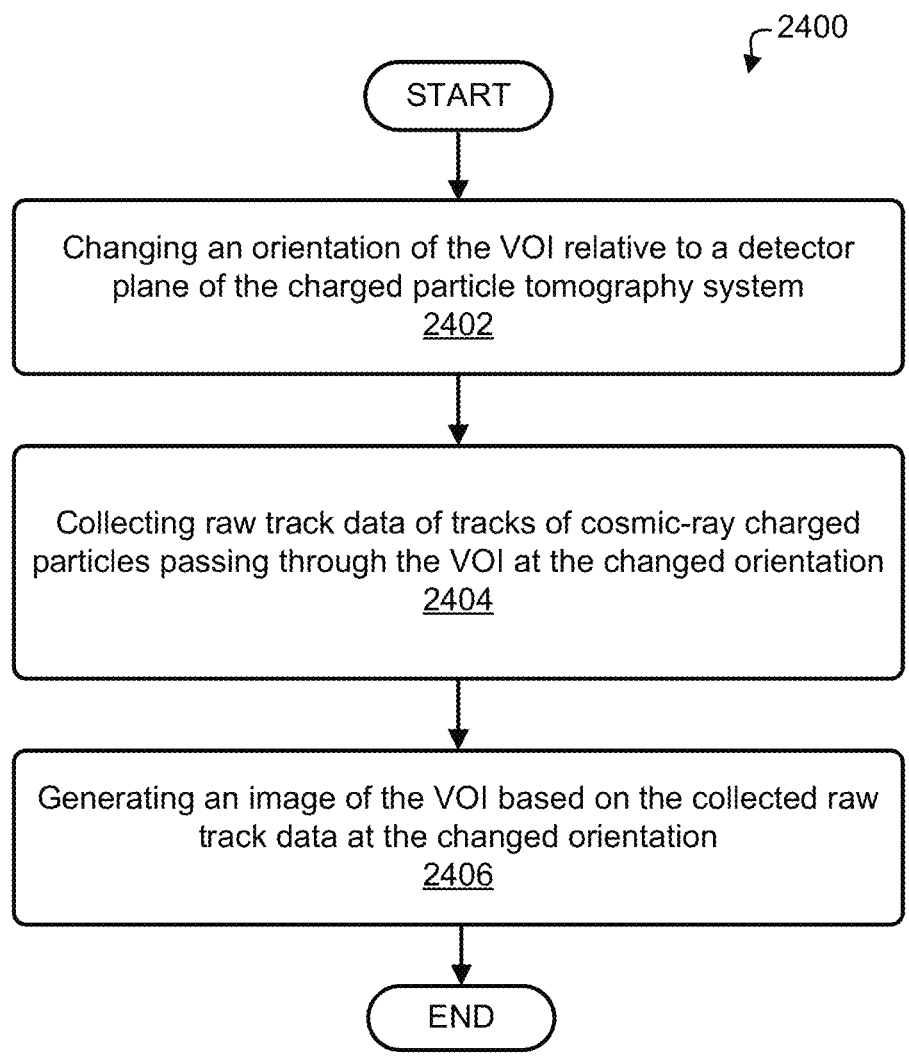
FIGS. 24A and 24B are process flow diagrams of a process for performing charged particle tomography imaging of a volume of interest (VOI) by a charged particle tomography system.
Figure 24B:
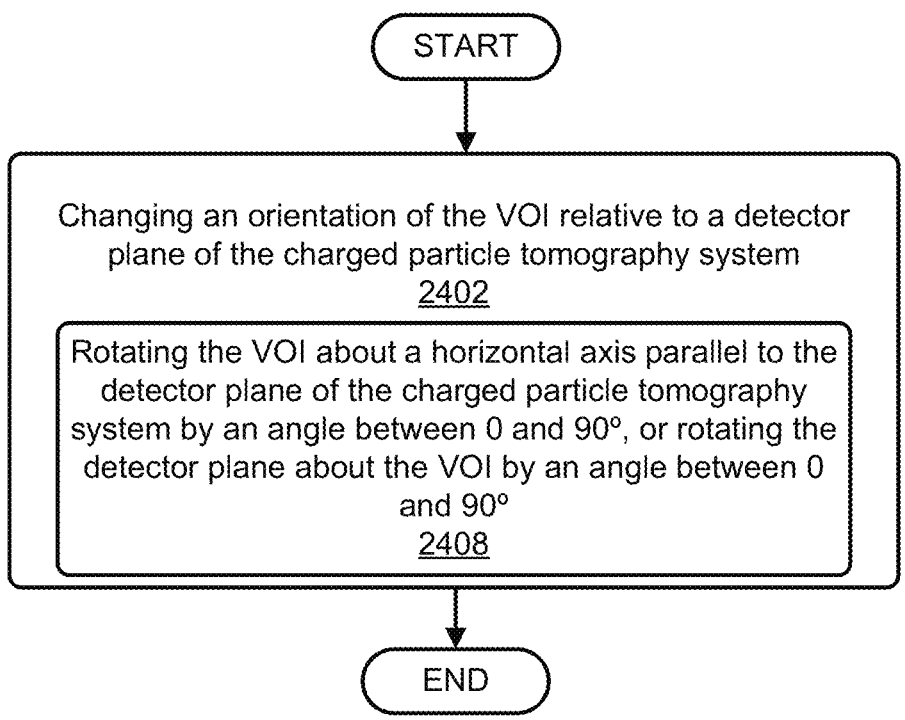

In another aspect, FIGS. 24A and 24B are process flow diagrams of a process 2400 for performing charged particle tomography imaging of a volume of interest (VOI) by a charged particle tomography system. The process includes changing an orientation of the VOI relative to a detector plane of the charged particle tomography system (2402). The process includes collecting raw track data of tracks of cosmic-ray charged particles passing through the VOI at the changed orientation (2404). The process includes generating an image of the VOI based on the collected raw track data at the changed orientation (2406). Changing the orientation of the VOI changes a zenith angular range of the tracks and changes a resolution of the generated image in a vertical direction perpendicular to the detector plane.

The process can be implemented to include one or more of the following features. For example, changing the orientation can include rotating the VOI about a horizontal axis parallel to the detector plane of the charged particle tomography system by an angle between 0 and 90°, or rotating the detector plane about the VOI by an angle between 0 and 90° (2408). The cosmic-ray charged particles can include muons.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method for generating charged particle tomography images for a volume of interest (VOI) by a charged particle tomography system, the method comprising:

collecting raw track data of tracks of cosmic-ray based charged particles passing through the VOI;

grouping the collected raw track data into subsets of the tracks based on angular distribution of the tracks in a zenith direction in the raw track data by partitioning the collected raw track data into a first subset corresponding to large zenith angles and a second subset corresponding to small zenith angles;

generating a set of images of the VOI based on the grouped subsets of the tracks; and combining information from at least the generated set of images to obtain an resulting image of the VOI.

2. The method of claim 1, comprising:

generating an image based on full set of the raw track data; and wherein the combining includes combining information from the generated image based on the full set of the raw track data along with the information from the generated set of images to obtain the resulting image of the VOI.

3. The method of claim 1, wherein the first subset of tracks has a zenith angle range from 0 to X and the second subset of tracks has a zenith angle range from X to 90°, wherein X is between 20° to 45° to achieve a distribution of muon counts in the first and second subsets that limits a noise level of the set of images.

4. The method of claim 3, comprising:

selecting X so that percentage of the tracks in the first subset and percentage of the tracks in the second subset have a predetermined relationship.

5. The method of claim 4, wherein the predetermined relationship includes the two percentages being substantially equal to each other.

6. The method of claim 3, wherein a first reconstructed image of the set of images based on the first subset of the tracks is associated with an object resolution in a horizontal direction parallel to a detector plane in the charged particle tomography system; and wherein a second reconstructed image based on the second subset of the tracks is associated with an object resolution in a vertical direction perpendicular to a detector plane in the charged particle tomography system.

7. The method of claim 6, wherein a third reconstructed image based on the full set of the raw track data is associated with an object resolution in the horizontal direction which is at a level between the object resolutions in the horizontal direction for the first reconstructed image and the second reconstructed image; and wherein the third reconstructed image based on the full set of the raw track data is associated with an object resolution in the vertical direction at a level between the resolutions in the vertical direction for the first reconstructed image and the second reconstructed image.

8. The method of claim 1, wherein grouping the raw track data into the subsets of the tracks based on the angular distribution includes:

identifying a subset of the tracks which are substantially perpendicular to a direction $\hat{u}$ in a detector plane of the charged particle tomography system.

9. The method of claim 8, wherein an image based on the identified subset of the tracks substantially perpendicular to the direction $\hat{u}$ is associated with an object resolution in the $\hat{u}$-direction.

10. The method of claim 1, wherein grouping the raw track data into the subsets of the tracks based on the angular distribution includes:
- partitioning the collected raw track data into a third subset corresponding to azimuthal angles, wherein the large zenith angles, the small zenith angles, and the azimuthal angles for the first, second, and third subsets respectively are within 45° of an x-direction in a detector plane of the charged particle tomography system; and
- partitioning the raw track data into a fourth subset corresponding to azimuthal angles which are within 45° of a y-direction in a detector plane of the charged particle tomography system.

11. The method of claim 1, wherein at least two of the subsets of the tracks share a common cosmic-ray based charged particle track.

12. The method of claim 1, wherein the cosmic-ray based charge particles include muons.

13. A method for generating charged particle tomography image for a volume of interest (VOI) by a charged particle tomography system, the method comprising:
- collecting raw track data of tracks of cosmic-ray charged particles passing through the VOI;
- generating an image of the VOI based on the raw track data;
- identifying an orientation of objects in the generated image of the VOI based on the raw track data;
- grouping the raw track data into subsets of the tracks based on the identified orientation, wherein grouping the raw track data into the subsets of the tracks includes partitioning the raw track data into a first subset corresponding to large zenith angles and a second subset corresponding to small zenith angles;
- generating a set of images of the VOI based on the subsets of the tracks; and
- combining information from the generated set of images of the VOI based on the subsets of the tracks and the generated image based on the full set of the track data to obtain a resulting image of the VOI associated with a resolution along the identified orientation.

14. The method of claim 13, wherein grouping the raw track data into the subsets of the tracks based on the identified orientation includes identifying a subset of the tracks substantially perpendicular to the identified orientation.

15. The method of claim 14, wherein an image of the set of images based on the identified subset of tracks substantially perpendicular to the identified orientation is associated with an object resolution in the identified orientation.

16. The method of claim 13, wherein the first subset of the tracks has a zenith angle range from 0 to X and the second subset of the tracks has a zenith angle range from X to 90°, wherein X is between 20° or 45°.

17. The method of claim 13, wherein a first image based on the first subset of tracks provides an improvement of an object resolution in a horizontal direction parallel to a detector plane in the charged particle tomography system; and wherein a second image based on the second subset of tracks provides an improvement of an object resolution in a vertical direction perpendicular to a detector plane in the charged particle tomography system.

18. The method of claim 13, wherein grouping the raw track data into the subsets of the tracks includes partitioning the raw track data into a first subset corresponding to azimuthal angles in a first range which are within 45° of an x-direction in a detector plane of the charged particle tomography system; and a second subset corresponding to azimuthal angles in a second range which are within 45° of a y-direction in the detector plane of the charged particle tomography system.

19. The method of claim 18, wherein a first reconstructed image based on the first subset of tracks is associated with an object resolution in the y-direction; and
- wherein a second reconstructed image based on the second subset of tracks is associated with an object resolution in the x-direction.

20. The method of claim 13, wherein the cosmic-ray charged particles include muons.

* * * * *

UNITED STATES PATENT AND TRADEMARK OFFICE
CERTIFICATE OF CORRECTION

PATENT NO. : 9,639,973 B2  
APPLICATION NO. : 14/678921  
DATED : May 2, 2017  
INVENTOR(S) : Chuanyong Bai et al.

Page 1 of 1

It is certified that error appears in the above-identified patent and that said Letters Patent is hereby corrected as shown below:

In the Specification

In Column 17, Line 25, delete "subset) (0°-24°," and insert --subset (0°-24°),--, therefor.

In Column 17, Line 26, delete "subset) (24°-90°," and insert --subset (24°-90°),--, therefor.

In Column 17, Lines 26-27, delete "dataset) (0°-90°'" and insert --dataset (0°-90°)--, therefor.

In Column 18, Line 53, delete "angle) (24°-90°'" and insert --angle (24°-90°)--, therefor.

In Column 18, Line 55, delete "angle) (0°-24°." and insert --angle (0°-24°).--, therefor.

In Column 19, Line 49, delete "angle) (0°-24°'" and insert --angle (0°-24°)--, therefor.

In Column 19, Line 51, delete "angle) (24°-90°'" and insert --angle (24°-90°)--, therefor.

In Column 23, Line 43, delete "it" and insert --û--, therefor.

In the Claims

In Column 28, Line 62, in Claim 8, delete "ûin" and insert --û in--, therefor.

Signed and Sealed this  
Nineteenth Day of November, 2019

Andrei Iancu  
*Director of the United States Patent and Trademark Office*